United States Patent [19]

Hassall et al.

[11] 4,302,398
[45] Nov. 24, 1981

[54] CYCLIC COMPOUNDS

[75] Inventors: Cedric H. Hassall, Hatfield; Michael J. Broadhurst, Baldock; Gareth J. Thomas, Luton, all of England

[73] Assignee: Hoffmann-La Roche Inc., Nutley, N.J.

[21] Appl. No.: 175,724

[22] Filed: Aug. 6, 1980

[30] Foreign Application Priority Data

Aug. 20, 1979 [GB] United Kingdom ............... 28889/79
Jul. 21, 1980 [GB] United Kingdom ............... 23715/80

[51] Int. Cl.$^3$ ................... C07C 50/16; C07C 107/02
[52] U.S. Cl. ................................. 260/365; 260/366; 260/383; 260/462 C; 260/691
[58] Field of Search .............. 260/366, 365, 276, 383, 260/462 C, 691

[56] References Cited

U.S. PATENT DOCUMENTS

| | | | |
|---|---|---|---|
| 3,287,270 | 11/1966 | McCabe et al. | 260/462 C |
| 4,077,988 | 3/1978 | Arcamone et al. | 260/376 |
| 4,107,423 | 8/1978 | Arcamone et al. | 260/365 |
| 4,132,721 | 1/1979 | Bernardi et al. | 260/365 |

FOREIGN PATENT DOCUMENTS 877874 9/1961 United Kingdom ............ 260/462 C

*Primary Examiner*—Winston A. Douglas
*Assistant Examiner*—Raymond K. Covington
*Attorney, Agent, or Firm*—Jon S. Saxe; Bernard S. Leon; Frank P. Hoffman

[57] ABSTRACT

The present invention relates to naphthacene derivatives. More particularly, the invention is concerned with a process for the manufacture of hexahydronaphthacene derivatives and with certain of said derivatives per se. The invention is also concerned with novel intermediates occurring in said process and with the preparation thereof.

There are presented hexahydronaphthacene derivatives of the formula

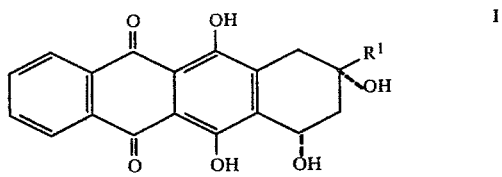

wherein $R^1$ represents a lower alkyl or esterified carboxy group or a group of the formula

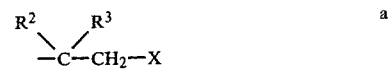

, in which $R^2$ and $R^3$ together form an oxo group or a protected oxo group and X represents a hydrogen atom or a hydroxy or acyloxy group, or

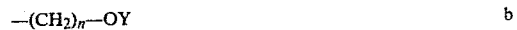

in which n stands for 1 or 2 and Y represents a hydrogen atom or an alkyl or acyl group.

Also presented are intermediates and a process to produce the compounds of formula I.

11 Claims, No Drawings

CYCLIC COMPOUNDS

DESCRIPTION OF THE INVENTION

The present invention relates to naphthacene derivatives. More particularly, the invention is concerned with a process for the manufacture of hexahydronaphthacene derivatives and with certain of said derivatives per se. The invention is also concerned with novel intermediates occurring in said process and with the preparation thereof.

The hexahydronaphthacene derivatives obtained in accordance with the present invention are compounds of the general formula

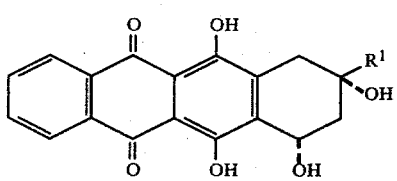

I wherein $R^1$ represents a lower alkyl or esterified carboxy group or a group of the formula

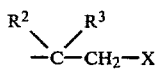

a in which $R^2$ and $R^3$ together form an oxo group or a protected oxo group and X represents a hydrogen atom or a hydroxy or acyloyx group, or

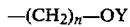   b in which n stands for 1 or 2 and Y represents a hydrogen atom or an alkyl or acyl group.

As used in this Specification, the term "lower alkyl" means a straight-chain or branched-chain alkyl group which preferably contains from 1 to 6 carbon atoms such as methyl, ethyl, propyl, isopropyl, butyl, tert.butyl, pentyl, hexyl etc. A protected oxo group herein can be any conventional protected oxo group. Preferably, an oxo group is protected in the form of a ketal or thioketal, especially an alkylene ketal or alkylene thioketal. An esterified carboxy group can be an alkoxycarbonyl group (e.g. methoxycarbonyl, ethoxycarbonyl etc), an aryloxycarbonyl group (e.g. phenoxycarbonyl etc) or an aralkoxycarbonyl group (e.g. benzyloxycarbonyl etc). The methoxycarbonyl group is the preferred alkoxycarbonyl group. An acyl group or the acyl moiety of an acyloxy group can be derived from an alkanecarboxylic acid (e.g. acetic acid, propionic acid etc), an aromatic carboxylic acid (e.g. benzoic acid etc) or an araliphatic carboxylic acid (e.g. phenylacetic acid etc). An aryl group can be, for example, phenyl, substituted-phenyl (e.g. methoxyphenyl), pyridyl etc.

According to the present invention, the hexahydronaphthacene derivatives of formula I hereinbefore are manufactured by subjecting a compound of the general formula

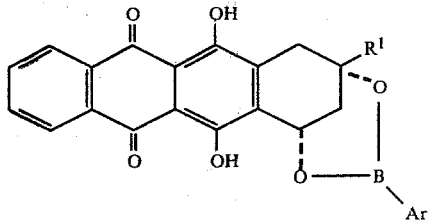

II wherein $R^1$ has the significance given earlier and Ar represents an aryl group,
to an ester-exchange with a 1,3-diol.

The aforementioned ester-exchange can suitably be carried out by reacting a compound of formula II with an excess of a 1,3-diol in the presence of an acid. An especially preferred 1,3-diol is 2-methyl-2,4-pentanediol. Preferred among the acids which can be used are the lower alkanecarboxylic acids such as acetic acid etc. The reaction is conveniently carried out in the presence of an inert organic solvent (e.g. a halogenated hydrocarbon such as dichloromethane etc.) and at about room temperature.

The compounds of formula II hereinbefore can be prepared, also in accordance with the present invention, by de-acylating a compound of the general formula

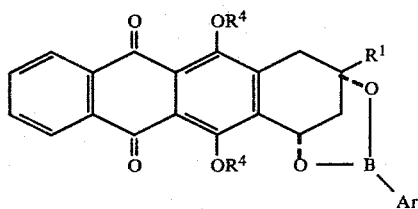

III wherein $R^1$ and Ar have the significance given earlier and $R^4$ represents an acyl group.

The de-acylation of a compound of formula III is preferably carried out using boron trichloride in an inert organic solvent (e.g. a halogenated hydrocarbon such as dichloromethane etc) and at a low temperature (e.g. at about $-10°$ C.). The de-acylation may also be carried out by aqueous acid or base treatment under conventional conditions.

The compounds of formula III hereinbefore can be prepared, also in accordance with the present invention, by oxidising a compound of the general formula

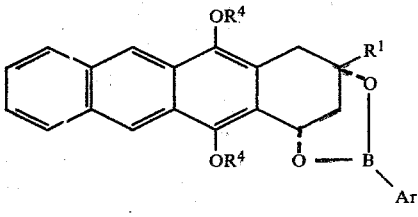

IV wherein $R^1$, $R^4$ and Ar have the significance given earlier,
with a chromic oxidising agent under anhydrous conditions.

A preferred chromic oxidising agent for use in the foregoing oxidation is chromium trioxide. In a preferred embodiment, this oxidation is carried out in the presence of a mixture of an appropriate anhydrous carboxylic acid and the anhydride corresponding thereto (e.g. a mixture of glacial acetic acid and acetic anhydride). This oxidation can be carried out at a temperature between about room temperature and about 60° C., preferably at about room temperature.

The compounds of formula IV hereinbefore can be prepared, also in accordance with the present invention, by catalytically hydrogenating a compound of the general formula

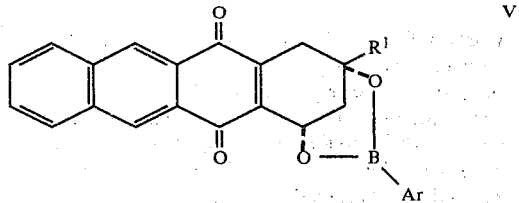

V wherein $R^1$ and Ar have the significance given earlier, under acylating conditions.

Suitable catalysts which may be used in the catalytic hydrogenation of a compound of formula V are noble metal catalysts such as, for example, palladium, platinum, ruthenium, rhodium etc. The catalyst may be supported on a suitable carrier material (e.g. palladium-on-carbon etc). The acylating conditions are provided by carrying out the catalytic hydrogenation in the presence of a suitable acylating agent, preferably a carboxylic acid anhydride such as acetic anhydride etc. A tertiary organic base is conveniently present in the mixture as an acid-binding agent. Included among the tertiary organic bases which can be used are tri(lower alkyl)amines such as triethylamine, pyridine, collidine etc. Pyridine is the preferred tertiary organic base. The catalytic hydrogenation is advantageously carried out at room temperature and at atmospheric pressure.

The compounds of formula V hereinbefore can be prepared, also in accordance with the present invention, by reacting a compound of the general formula

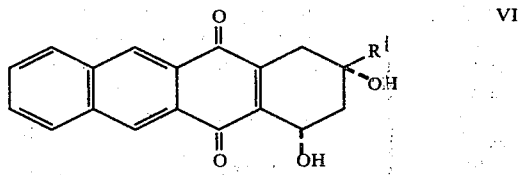

VI wherein $R^1$ has the significance given earlier, with an aromatic boronic acid.

The reaction of a compound of formula VI with an aromatic boronic acid is preferably carried out in an inert organic solvent. The preferred solvents are aromatic hydrocarbons such as benzene, toluene and xylene. Of the aromatic boronic acids which can be used in this reaction benzeneboronic acid is preferred. However, other aromatic boronic acids such as tolueneboronic acid, xyleneboronic acid, methoxybenzeneboronic acid, nitrobenzeneboronic acid, pyridineboronic acid or the like can also be used. It is convenient to carry out this reaction in the presence of a catalytic amount of a carboxylic acid, preferably a lower alkanecarboxylic acid such as acetic acid, propionic acid etc. The reaction is advantageously carried out at an elevated temperature, suitably at the reflux temperature of the reaction mixture.

It will be appreciated that, depending on the conditions used in carrying out the process steps described hereinbefore, certain substituents falling within the definition of R may be converted into different substituents. Thus, for example, an acyloxy group may be hydrolysed to a hydroxy group, a hydroxy group may be acylated to an acyloxy group or a protected oxo group may be transformed into an oxo group. When such conversions occur and the original substituents is required in the product, said substituent can be regenerated in accordance with methods known per se after the particular process step has been carried out or at an appropriate later stage in the overall process.

The compounds of formula VI hereinbefore can be prepared, for example, as shown in Formula Scheme I hereinafter in which $R^1$ has the significance given earlier and $R^5$ represents an acyloxy group.

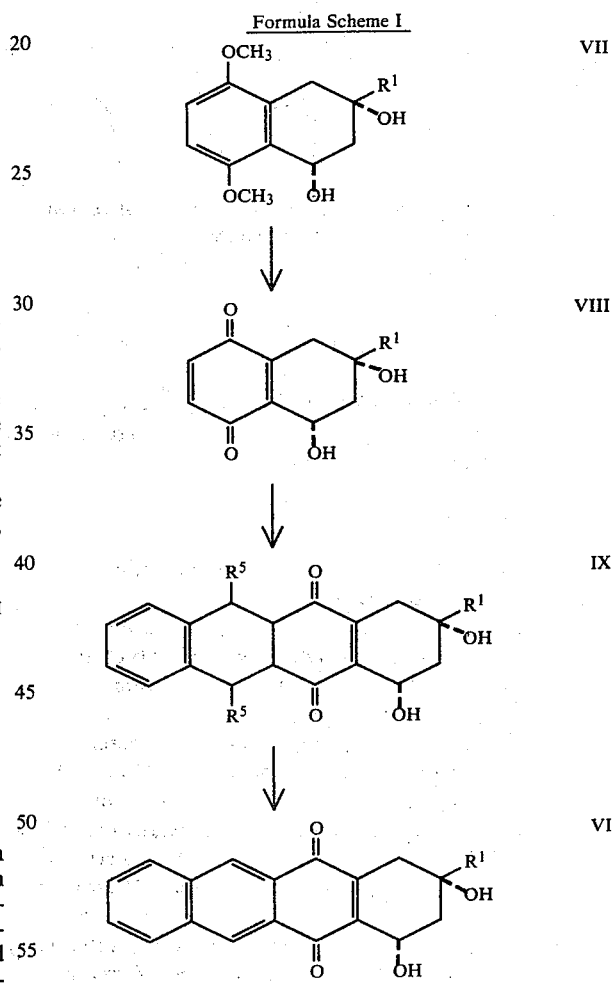

Having regard to the Formula Scheme I, a compound of formula VII is converted into a compound of formula VIII by treatment with ammonium ceric nitrate. This treatment is advantageously carried out in a mixture of water and a water-miscible organic solvent (e.g. acetonitrile or the like). The treatment is advantageously carried out at about room temperature.

A compound of formula VIII is then converted into a compound of formula IX by reaction with a trans compound of the general formula

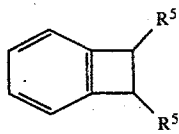

wherein $R^5$ has the significance given earlier.

The reaction of a compound of formula VIII with a trans compound of formula X to give a compound of formula IX is suitably carried out in an inert organic solvent, especially an aromatic hydrocarbon such as benzene, toluene or xylene. It is preferred to carry out this reaction at an elevated temperature, conveniently at the reflux temperature of the reaction mixture. If desired, the reaction can be carried out under the atmosphere of an inert gas such as nitrogen or argon.

2 mols of the carboxylic acid $R^5H$ are then eliminated from a compound of formula IX by heating or treatment with a base, there being obtained a compound of formula VI. The heating of a compound of formula IX is preferably carried out in an inert organic solvent. Preferred among the solvents which can be used for this purpose are aromatic hydrocarbons such as benzene, toluene and xylene. The heating is preferably carried out at the reflux temperature of the mixture. If desired, the heating may be carried out under the atmosphere of an inert gas such as nitrogen or argon. Preferably, a compound of formula IX is heated in situ; that is to say, without isolation from the medium in which it is prepared. The treatment of a compound of formula IX with a base can be carried out using an inorganic base or an organic base. It is preferred to carry out this treatment using an inorganic base, particularly an alkali metal hydroxide such as sodium hydroxide or potassium hydroxide, in a lower alkanol (e.g. methanol or ethanol). This treatment is conveniently carried out at about room temperature.

The compounds of formula VII hereinbefore can be prepared, in turn, from a cis/trans compound corresponding to formula VII. Thus, such a cis/trans compound can be treated with an aromatic boronic acid to give a mixture of the cis boronic acid ester and unchanged trans diol. This mixture can be separated and the cis boronic acid ester can be converted into the cis diol. The treatment with an aromatic boronic acid such as one of those mentioned hereinbefore, preferably benzeneboronic acid, is expediently carried out in an inert organic solvent such as ethyl acetate at an elevated temperature, suitably at the reflux temperature of the mixture, and, if desired, under the atmosphere of an inert gas such as nitrogen or argon. The separation of the cis boronic acid ester and trans diol can be carried out by chromatography, suitably on silica gel. The cis boronic acid ester is conveniently converted into the cis diol by treatment with an acid, preferably an organic carboxylic acid such as acetic acid, in the presence of an excess of a 1,3-diol such as 2-methyl-2,4-pentanediol. The treatment is conveniently carried out in an inert organic solvent, preferably a halogenated hydrocarbon such as dichloromethane, and at room temperature.

A trans diol can be converted into a corresponding cis boronic acid ester which, in turn, can be converted into the cis diol. The conversion of the trans diol into the cis boronic acid ester can be carried out by treatment with an aromatic boronic acid such as one of those mentioned earlier, preferably benzeneboronic acid, in the presence of an organic sulphonic acid, preferably an aromatic sulphonic acid such as toluene-4-sulphonic acid. This treatment is advantageously carried out in an inert organic solvent, preferably an aromatic hydrocarbon such as benzene, at about room temperature. This cis boronic acid ester obtained can then be converted into the cis diol in the manner described earlier.

Formula Scheme II hereinafter illustrates the preparation of cis/trans compounds corresponding to formula VII in which $R^1$ represents a group of formula (a) hereinbefore wherein $R^2$ and $R^3$ together represent an alkylenedioxy group and X represents a hydrogen atom. In this Formula Scheme, $R^{20}$ and $R^{30}$ together represent an alkylenedioxy group, especially the ethylenedioxy group, and $R^6$ and $R^7$ together represent an alkylenedioxy group, especially the ethylenedithio group.

Formula Scheme II

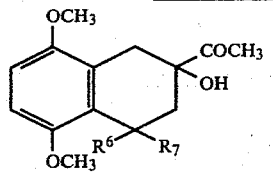 XI

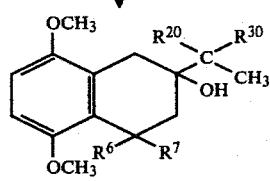 XII

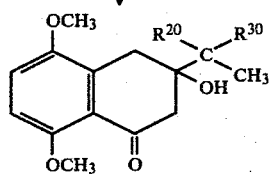 XIII

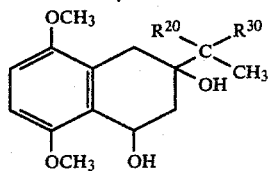 VIIa

Having regard to Formula Scheme II, a compound of formula XI prepared, for example, as described hereinafter, is treated with an alkyleneglycol, preferably ethyleneglycol, in the presence of toluene-4-sulphonic acid to give a compound of formula XII. This treatment can be carried out under the same conditions as described hereinafter in connection with the conversion of a compound of formula XIV into a compound of formula XV.

A compound of formula XII is then converted into a compound of formula XIII by treatment with a mercuric salt, preferably a mixture of mercuric chloride and mercuric oxide. This treatment is suitably carried out in a water-miscible inert organic solvent such as an alkanol (e.g. methanol, ethanol etc), tetrahydrofuran etc or in a mixture of such solvents which may also contain water. The treatment is preferably carried out at room temperature.

A compound of formula XIII is subsequently reduced in a manner known per se to give a compound of formula VIIa. This reduction is conveniently carried out using an alkali metal borohydride, preferably lithium borohydride, in a customary inert organic solvent such as tetrahydrofuran. Conveniently, this reduction is carried out at room temperature. If desired, the reduction can be carried out under the atmosphere of an inert gas such as nitrogen or argon.

Compounds of formula XI in Formula Scheme II can be prepared as shown in Formula Scheme III hereinafter in which $R^6$ and $R^7$ have the significance given earlier, $R^{10}$ represents an esterified carboxy group and $R^{60}$ and $R^{70}$ each represent an alkylenedioxy group, especially the ethylenedioxy group.

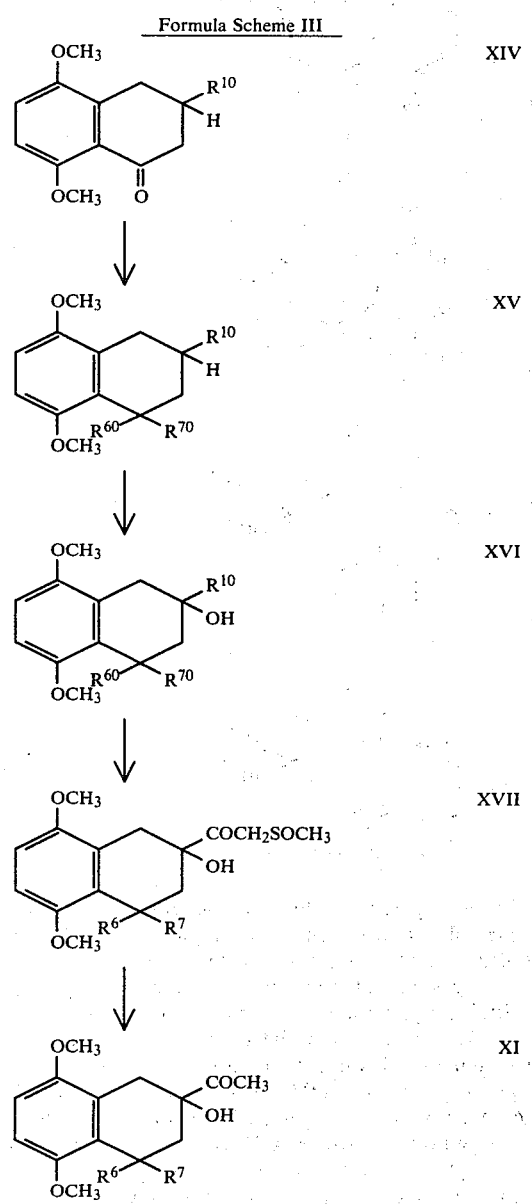

Formula Scheme III

Having regard to Formula Scheme III, a compound of formula XIV, which is a known compound or an analogue of a known compound, is converted into a compound of formula XV in a manner known per se for the ketalisation of an oxo group. This ketalisation can be carried out, for example, using an appropriate alcohol in the presence of toluene-4-sulphonic acid and in the presence of a suitable inert organic solvent such as an aromatic hydrocarbon (e.g. benzene, toluene etc) at an elevated temperature (e.g. at the reflux temperature of the reaction mixture).

A compound of formula XV is converted into a compound of formula XVI by first forming the lithium enolate of a compound of formula XV and then treating the enolate either with diperoxo-oxohexamethylphosphoramidomolybdenum (VI) pyridine (MoO$_5$.-py.HMPT) or with oxygen in the presence of a trialkylphosphite.

The conversion of a compound of formula XV into a lithium enolate is carried out in a manner known per se; for example, using lithium diisopropylamide in an inert organic solvent such as tetrahydrofuran at a low temperature (e.g. −78° C.).

The lithium enolate is then treated, preferably in situ, either with the diperoxo-oxohexamethylphosphoramidomolybdenum (VI) pyridine, suitably at a temperature between about room temperature and −78° C., or with oxygen in the presence of a trialkylphosphite (e.g. triethylphosphite), suitably by passing oxygen gas through a mixture of the enolate and the trialkylphosphite in an inert organic solvent such as tetrahydrofuran at a low temperature (e.g. −78° C.).

A compound of formula XVI is then converted into a compound of formula XVII. Firstly, the alkylenedioxy group denoted by $R^{60}$ and $R^{70}$ together in a compound of formula XVI is replaced by an alkylenedithio group, especially the ethylenedithio group. This replacement can be carried out by treating the alkylenedioxy-substituted compound with an appropriate alkanedithiol (e.g. ethanedithiol) in the presence of boron trifluoride etherate. This treatment is suitably carried out in an inert organic solvent such as a halogenated hydrocarbon (e.g. dichloromethane) at a temperature of about 0° C. The resulting compound is then converted into a β-ketosulphoxide of formula XVII by treatment with an alkali metal salt of dimethyl sulphoxide. This treatment is preferably carried out using the sodium salt of dimethyl sulphoxide and in an inert organic solvent (e.g. tetrahydrofuran) at about 0° C.

A compound of formula XVII is then converted into a compound of formula XI by treatment with aluminium amalgam. This treatment is suitably carried out in the presence of an inert solvent (e.g. aqueous tetrahydrofuran) at a temperature between about 10° C. and 20° C. If desired, this treatment can be carried out under the atmosphere of an inert gas such as nitrogen or argon.

Cis/trans compounds corresponding to formula VII in which $R^1$ represents a group of formula (b) wherein n stands for 1 can be prepared, for example, by reducing a compound of the general formula

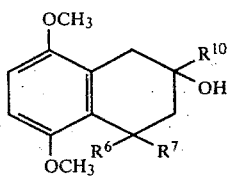

XVIII wherein R⁶, R⁷ and R¹⁰ have the significance given earlier,
in a manner known per se to give a compound of the general formula

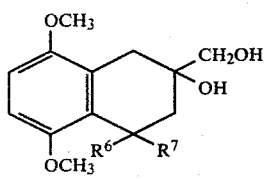

XIX wherein R⁶ and R⁷ have the significance given earlier, if desired, appropriately etherifying or acylating a compound of formula XIX to give a compound of the general formula

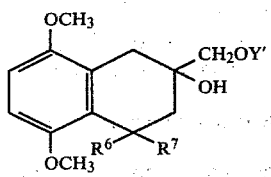

XX wherein R⁶ and R⁷ have the significance given earlier and Y' represents an alkyl or acyl group,
treating a compound of formula XIX or XX with a mercuric salt to give a compound of the general formula

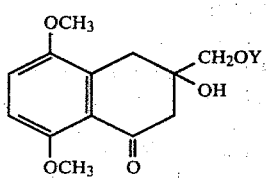

XXI wherein Y has the significance given earlier,
and reducing a compound of formula XXI.

The reduction of a compound of formula XVIII, which can be prepared as described earlier from a compound of formula XVI, can be carried out, for example, using an alkali metal borohydride such as sodium borohydride in an inert organic solvent such as tetrahydrofuran etc.

The optional etherification of a compound of formula XIX can be carried out in a manner known per se; for example, with an alkyl halide (e.g. methyl iodide) in the presence of a base (e.g. sodium hydride) and in an inert organic solvent such as dioxan, tetrahydrofuran, 1,2-dimethoxyethane etc. The optional acylation of a compound of formula XIX can also be carried out in a manner known per se.

The treatment of a compound of formula XIX or XX with a mercuric salt can be carried out in an analogous manner to that described earlier in connection with the conversion of a compound of formula XII into a compound of formula XIII.

The reduction of a compound of formula XXI can be carried out in a manner analogous to that described earlier in connection with the reduction of a compound of formula XIII to give a compound of formula VIIa.

Cis-trans compounds corresponding to formula VII in which R¹ represents a group of formula (b) wherein n stands for 2 and Y represents a hydrogen atom can be prepared, for example, by first converting a compound of formula XIX into a compound of the general formula

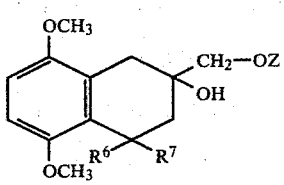

XXII wherein R⁶ and R⁷ have the significance given earlier and Z represents a lower alkylsulphonyl or arylsulphonyl group.

This conversion can be carried out in a manner known per se; for example, by reaction with a lower alkylsulphonyl chloride (e.g. methanesulphonyl chloride) or, preferably, with an arylsulphonyl chloride (e.g. toluene-4-sulphonyl chloride) in the presence of an appropriate base (e.g. a tertiary amine such as pyridine, 4-dimethylaminopyridine etc) and at a low temperature (e.g. 0°–5° C.).

In the next step, a compound of formula XXII is treated with an alkali metal cyanide to give a compound of the general formula

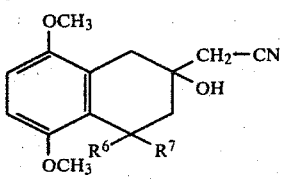

XXIII wherein R⁶ and R⁷ have the significance given earlier. This treatment is carried out in a known manner; for example, using potassium cyanide in aqueous dimethyl sulphoxide or dimethylformamide.

A compound of formula XXIII is then hydrolysed to give a compound of the general formula

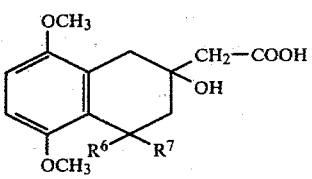

XXIV wherein R⁶ and R⁷ have the significance given earlier. This hydrolysis is carried out in a manner known per se for the hydrolysis of nitriles to the corresponding acids; for example, using an alkali metal hydroxide such as potassium hydroxide in an aqueous lower alkanol such as aqueous ethanol.

A compound of formula XXIV is then reduced to give a compound of the general formula

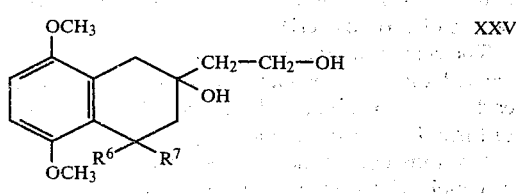

wherein $R^6$ and $R^7$ have the significance given earlier. This reduction can be carried out in a manner known per se for the reduction of carboxylic acids to corresponding alcohols. Thus, for example, the reduction can be carried out using an alkali metal aluminium hydride (e.g. lithium aluminium hydride) in an inert organic solvent (e.g. tetrahydrofuran, dioxan etc). Again, for example, the reduction can be carried out using diborane. In certain circumstances it can be advantageous to convert a compound of formula XXIV into an ester (e.g. the methyl ester) prior to the reduction.

A compound of formula XXV is subsequently subjected to optional etherification or acylation, treatment with a mercuric salt and reduction in a manner analogous to that described earlier to give a cis/trans compound corresponding to formula VII in which $R^1$ represents a group of formula (b) wherein n stands for 2.

Cis/trans compounds corresponding to formula VII in which $R^1$ represents a methyl group can be prepared, for example, by reducing a compound of formula XXII with an alkali metal aluminium hydride such as lithium aluminium hydride in a known manner followed by treatment with a mercuric salt and reduction as described earlier. Cis/trans compounds corresponding to formula VII in which $R^1$ represents a different lower alkyl group can be prepared similarly from corresponding ω-(lower alkylsulphonyloxy or arylsulphonyloxy)-(lower alkyl) compounds. For example, from a lower alkylsulphonate or aryl sulphonate derived from a compound of formula XXV there can be obtained a cis/trans compound corresponding to formula VII in which $R^1$ represents an ethyl group. Alternatively, this lower alkylsulphonate or arylsulphonate can be chain-lengthened according to the procedure described earlier (i.e. via a nitrile, acid and alcohol). This chain-lengthening can, of course, be repeated as required.

Compounds of formulae I, II, III, IV, V and VI hereinbefore can exist not only in racemic but also in optically active form. It will be appreciated that the invention includes not only the racemates but also the optical isomers. A racemate can be split up into its optical isomers in accordance with methods known per se. For example, a compound in which $R^1$ represents an esterified carboxy group can be saponified to the corresponding carboxylic acid (e.g. by treatment with an alkali metal hydroxide such as sodium hydroxide) and the acid can be resolved by salt formation with an appropriate base such as brucine. An optically active acid thus obtained can subsequently be esterified to give a corresponding optically active ester.

It will be appreciated that when an optically active starting material is used in the process of this invention, the optical configuration is retained during the entire reaction sequence, thus enabling the preparation of isomers with specific chirality at the chiral centre(s) present.

The compounds of formula I hereinbefore (provided that $R^2$ and $R^3$ together represent a protected oxo group when X represents a hydrogen atom or a hydroxy group) and the compounds of formulae II, III and IV hereinbefore also form part of the present invention.

The compounds of formula I hereinbefore are useful as chemical intermediates; for example, in the manufacture of other tetracyclic compounds having antibiotic activity or antitumour activity. Thus, for example, compounds of formula I can be converted into compounds of the general formula

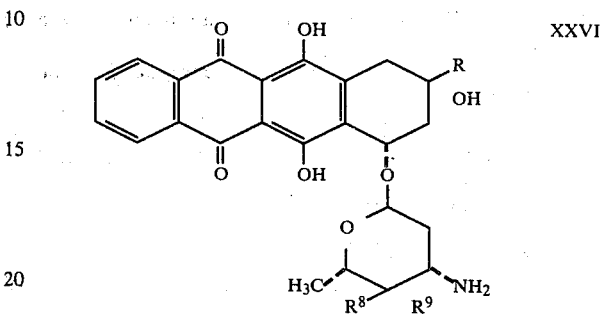

wherein R represents a lower alkyl or carboxy group, a group of formula (a) hereinbefore in which $R^2$ and $R^3$ together form an oxo group and X represents a hydrogen atom or a hydroxy group or a group of formula (b) hereinbefore in which Y represents a hydrogen atom or an alkyl group and $R^8$ and $R^9$ each represent a hydrogen atom or one of $R^8$ and $R^9$ represents a hydrogen atom and the other represents a hydroxy group, and pharmaceutically acceptable acid addition salts thereof.

The conversion of compounds of formula I into compounds of formula XXVI and their pharmaceutically acceptable acid addition salts, which are partly known and partly novel, can be carried out as described in the following Examples or in analogy thereto.

The following Examples illustrate the present invention:

EXAMPLE 1

(A) A solution of 760 mg (2 mmol) of rac-cis-3-(1,1-ethylenedioxyethyl)-1,2,3,4,5,12-hexahydro-5,12-dioxonaphthacene-1,3-diol and 244 mg (2 mmol) of benzeneboronic acid in a mixture of 150 ml of benzene and 0.5 ml of glacial acetic acid was stirred and heated under reflux for 1 hour. The mixture was left to cool and the solvent was removed by evaporation to give a yellow residue. This residue was triturated with 50 ml of diethyl ether and filtered to give 830 mg (89%) of rac-cis-3-(1,1-ethylenedioxyethyl)-1,2,3,4,5,12-hexahydro-5,12-dioxo-1,3-naphthacenediyl benzene-boronate in the form of a bright yellow solid of melting point 239°–241° C.

(B) 830 mg (1.78 mmol) of rac-cis-3-(1,1-ethylenedioxyethyl)-1,2,3,4,5,12-hexahydro-5,12-dioxo-1,3-naphthacenediyl benzeneboronate were dissolved in a mixture of 40 ml of dry pyridine and 20 ml of acetic anhydride. 10% palladium-on-carbon was added and the mixture was hydrogenated at room temperature and atmospheric pressure for 0.5 hour. The catalyst was removed by filtration and the filtrate was diluted with 160 ml of dichloromethane. The resulting solution was washed with three 200 ml portions of water, dried over anhydrous sodium sulphate, filtered and evaporated. The residue was triturated with diethyl ether and filtered to give 970 mg (99%) of rac-cis-5,12-diacetoxy-3-

(1,1-ethylenedioxyethyl)-1,2,3,4-tetrahydro-1,3-naphthacenediyl benzeneboronate in the form of a pale yellow solid of melting point 282°–283° C. After recrystallisation from acetone, the melting point increased to 287°–292° C.

(C) 331 mg (0.6 mmol) of rac-cis-5,12-diacetoxy-3-(1,1-ethylenedioxyethyl)-1,2,3,4-tetrahydro-1,3-naphthacenediyl benzeneboronate were dissolved in a mixture of 18 ml of glacial acetic acid and 6 ml of acetic anhydride. 240 mg (2.4 mmol) of finely ground chromium trioxide were added and the mixture was stirred at room temperature for 16 hours. The mixture was then poured into 250 ml of water and the resulting suspension was extracted with two 200 ml portions of dichloromethane. The combined dichloromethane extracts were evaporated and the residue was triturated with diethyl ether and filtered to give 110 mg of rac-cis-5,12-diacetoxy-3-(1,1-ethylenedioxyethyl)-1,2,3,4,6,11-hexahydro-6,11-dioxo-1,3-naphthacenediyl benzeneboronate in the form of a pale yellow solid of melting point 210°–220° C. Concentration of the diethyl ether mother liquor gave a second crop weighing 100 mg. The total yield of product was 210 mg (60%).

(D) A solution of 100 mg (0.17 mmol) of rac-cis-5,12-diacetoxy-3-(1,1-ethylenedioxyethyl)-1,2,3,4,6,11-hexahydro-6,11-dioxo-1,3-naphthacenediyl benzeneboronate in 20 ml of dichloromethane was stirred and cooled to −78° C. A solution of 125 mg of boron trichloride in 5 ml of dichloromethane was added and the mixture was stirred and left to warm to −10° C. over a period of 1 hour. The mixture was then poured into 20 ml of ice-cold 2-M hydrochloric acid and the layers were separated. The organic layer was washed with 20 ml of water, dried over anhydrous sodium sulphate, filtered and the filtrate was evaporated. The residue was triturated with 5 ml of diethyl ether and filtered to give 60 mg (77%) of rac-cis-3-acetyl-1,2,3,4,6,11-hexahydro-5,12-dihydroxy-6,11-dioxo-1,3-naphthacenediyl benzeneboronate in the form of a bright red solid of melting point 215°–223° C.

(E) 45 mg (0.10 mmol) of rac-cis-3-acetyl-1,2,3,4,6,11-hexahydro-5,12-dihydroxy-6,11-dioxo-1,3-naphthacenediyl benzeneboronate were dissolved in 6 ml of dichloromethane. 1.5 ml of 2-methyl-2,4-pentanediol and 0.25 ml of glacial acetic acid were added and the resulting solution was stirred at room temperature for 40 hours. The solution was then washed with three 15 ml portions of water, dried over anhydrous sodium sulphate, filtered and the solvent was removed by evaporation. The oily crystalline residue was triturated with diethyl ether and filtered to give 25 mg (69%) of rac-cis-3-acetyl-1,2,3,4,6,11-hexahydro-1,3,5,12-tetrahydroxy-6,11-dioxonaphthacene in the form of a bright red solid of melting point 125°–130° C. After recrystallisation from a mixture of dichloromethane and diethyl ether, the melting point increased to 172°–176° C.

The rac-cis-3-(1,1-ethylenedioxyethyl)-1,2,3,4,5,12-hexahydro-5,12-dioxonaphthacene-1,3-diol used as the starting material in part (A) of this Example can be prepared as follows:

(i) 40 g of methyl rac-1,2,3,4-tetrahydro-5,8-dimethoxy-4-oxonaphthalene-2-carboxylate were added to a mixture of 800 ml of toluene, 800 ml of hexane, 30 ml of ethyleneglycol and 0.65 g of toluene-4-sulphonic acid. The mixture was heated under reflux for 24 hours using a Dean-Stark trap. The solution was cooled in an ice-bath and washed with three 124 ml portions of 10% potassium hydrogen carbonate solution and 200 ml of brine, dried and the solvent was evaporated. The residue was taken up in 200 ml of methanol at 70° C. and 0.5 g of a 50% dispersion of sodium hydride in mineral oil was added. The solution obtained was left to cool to room temperature and then cooled further in an ice-bath for 2 hours. The crystalline product was filtered off, washed with cold methanol and dried in vacuo. There were obtained 28.5 g (61%) of methyl rac-4,4-ethylene-dioxy-1,2,3,4-tetrahydro-5,8-dimethoxynaphthalene-2-carboxylate in the form of colourless crystals of melting point 133°–134° C.

(ii) (a) To a solution of 84 ml of diisopropylamine in 250 ml of dry tetrahydrofuran at −78° C. under argon was added a solution of n-butyl lithium (39 ml, 1.6 mol) in hexane. The mixture was stirred for 10 minutes and then a solution of 12.32 g of methyl 4,4-ethylenedioxy-1,2,3,4-tetrahydro-5,8-dimethoxynaphthalene-2-carboxylate in 75 ml of dry tetrahydrofuran was added rapidly. The mixture was held at −78° C. while stirring for 50 minutes and then 27.8 g of finely ground diperoxo-oxohexamethylphosphoramidomolybdenum (VI) pyridine were added. After a further 80 minutes, the mixture was warmed to 0° C. and stirred for 20 minutes before the addition of 400 ml of water. After 10 minutes, most of the tetrahydrofuran was evaporated in vacuo and the aqueous residue was extracted with five 200 ml portions of ethyl acetate. The combined ethyl acetate extracts were dried over magnesium sulphate, filtered and evaporated to give an oil which was purified by chromatography on silica gel using ethyl acetate/hexane (1:1, vol/vol) for the elution. After the elution of 1.57 g of starting material, there were obtained 7.51 g (58%) of methyl rac-4,4-ethylenedioxy-1,2,3,4-tetrahydro-2-hydroxy-5,8-dimethoxynaphthalene-2-carboxylate in the form of colourless crystals of melting point 74°–75° C.

(ii) (b) A solution of the lithium enolate of methyl rac-4,4-ethylenedioxy-1,2,3,4-tetrahydro-5,8-dimethoxynaphthalene-2-carboxylate was prepared in tetrahydrofuran as described in part (ii) (a) hereinbefore from 9.84 g of methyl rac-4,4-ethylenedioxy-1,2,3,4-tetrahydro-5,8-dimethoxynaphthalene-2-carboxylate. The enolate was added over a period of 5 minutes at −78° C. to a stirred solution of 11.2 ml of dry triethylphosphite in 60 ml of tetrahydrofuran through which a rapid stream of oxygen was passing. The passage of oxygen was maintained for 50 minutes and the temperature was held at −78° C. The reaction was then quenched by the addition of 8.8 ml of acetic acid. The cooling bath was removed and, after 5 minutes, 200 ml of water were added. After a further 20 minutes, most of the tetrahydrofuran was evaporated and the product was extracted into four 100 ml portions of ethyl acetate. The combined ethyl acetate extracts were washed with 200 ml of 10% aqueous potassium hydrogen carbonate, dried over magnesium sulphate, filtered and evaporated to give a yellow oil which was dissolved in 130 ml of ether and left to crystallise. There were obtained 6.86 g (66%) of methyl rac-4,4-ethylenedioxy-1,2,3,4-tetrahydro-2-hydroxy-5,8-dimethoxynaphthalene-2-carboxylate in the form of colourless crystals of melting point 74°–75° C.

(iii) 10 g of methyl rac-4,4-ethylenedioxy-1,2,3,4-tetrahydro-2-hydroxy-5,8-dimethoxynaphthalene-2-carboxylate were dissolved in 30 ml of dichloromethane and the solution was cooled to 0° C. To the solution were added 4 ml of ethanedithiol followed by 4 ml of boron trifluoride etherate. The mixture was stirred at 0°

C. for 15 minutes and then poured into 200 ml of diethyl ether. The organic layer was washed with three 50 ml portions of 5% sodium hydroxide solution and evaporated to give a yellow oil which was taken up in 200 ml of methanol. 100 ml of 5% sodium hydroxide solution were added and the resulting solution was stirred at room temperature for 1.5 hours. Most of the methanol was then evaporated, the residue was diluted with 250 ml of water and washed with three 100 ml portions of ether. The aqueous layer was acidified with hydrochloric acid and the precipitated oil was left to solidify. The product was collected by filtration, washed free from acid using water and dried. The crude acid was purified by suspension in 150 ml of ethyl acetate and heating under reflux for 30 minutes. The mixture was cooled and the product was collected by filtration after 24 hours. There were obtained 7.0 g (66.5%) of 1',2',3',4'-tetrahydro-2'-hydroxy-5',8'-dimethoxyspiro[1,3-dithiolane-2,4'-naphthalene]-2'-carboxylic acid in the form of colourless crystals of melting point 189°–189.5° C.

(iv) 20 g of rac-1',2',3',4'-tetrahydro-2'-hydroxy-5',8'-dimethoxyspiro[1,3-dithiolane-2,4'-naphthalene]-2'-carboxylic acid were suspended in 200 ml of methanol and 40 ml of boron trifluoride/methanol were added. The mixture was stirred at room temperature for 3.5 hours to give a clear solution. Approximately 80 ml of methanol were removed by evaporation and the remaining solution was poured into 400 ml of dichloromethane. The organic solution was washed with 500 ml of water, 200 ml of 10% potassium hydrogen carbonate solution and 200 ml of brine. After drying over magnesium sulphate, the solvent was removed to give 24 g of a yellow gum. Crystallisation of this gum from diethyl ether/hexane gave 19.5 g (95.5%) of methyl rac-1',2',3',4'-tetrahydro-2'-hydroxy-5',8'-dimethoxyspiro[1,3-dithiolane-2,4'-naphthalene]-2'-carboxylate of melting point 103.5°–104° C.

(v) 2.55 g of a 50% dispersion of sodium hydride in mineral oil were added to 30 ml of dry dimethyl sulphoxide stirred under nitrogen. The mixture was stirred at 70° C. until the evolution of hydrogen ceased. After cooling to 0° C., 30 ml of dry tetrahydrofuran were added. 4.0 g of methyl rac-1',2',3',4'-tetrahydro-2'-hydroxy-5',8'-dimethoxyspiro[1,3-dithiolane-2,4'-naphthalene]-2'-carboxylate in 30 ml of dry tetrahydrofuran were added dropwise over a period of 10 minutes. After stirring at 0° C. for 15 minutes, the mixture was poured into 200 ml of water and acidified to pH 3 with hydrochloric acid. The solution was extracted with five 100 ml portions of dichloromethane. The combined dichloromethane extracts were washed with 200 ml of water, dried over magnesium sulphate and evaporated to give an orange solid. Trituration of this solid with a mixture of ethyl acetate and diethyl ether gave 3.5 g of crude β-ketosulphoxide in the form of a buff solid which was used without further purification.

3.5 g of the crude β-ketosulphoxide obtained as described in the preceding paragraph were dissolved in 150 ml of tetrahydrofuran containing 15 ml of water. The solution was stirred under nitrogen and cooled to 12° C. Aluminium amalgam (prepared from 3.5 g of aluminium foil) was added and the mixture was stirred for 2 hours while holding the temperature at 12°–15° C. The mixture was then filtered and the tetrahydrofuran was evaporated. The residue was dissolved in ethyl acetate, washed with water, dried and evaporated to give a cream coloured solid. Recrystallisation from dichloromethane/diethyl ether gave 2.5 g (66%) of rac-3'-acetyl-1',2',3',4'-tetrahydro-3'-hydroxy-5',8'-dimethoxyspiro[1,3-dithiolane-2,1'-naphthalene] in the form of colourless crystals of melting point 152.5°–153° C.

(vi) 2.0 g of rac-3'-acetyl-1',2',3',4'-tetrahydro-3'-hydroxy-5',8'-dimethoxyspiro[1,3-dithiolane-2,1'-naphthalene] were dissolved in 150 ml of benzene containing 15 ml of ethyleneglycol, 80 mg of toluene-4-sulphonic acid and 5 ml of acetone. The mixture was heated under reflux for 6 hours using a Dean-Stark water separator and then cooled to room temperature. The mixture was washed with two 100 ml portions of 10% aqueous potassium hydrogen carbonate and two 100 ml portions of water, dried over magnesium sulphate and evaporated to give a white foam. Trituration with diethyl ether gave rac-3'-(1,1-ethylenedioxyethyl)-1',2',3',4'-tetrahydro-3'-hydroxy-5',8'-dimethoxyspiro[1,3-dithiolane-2,1'-naphthalene] in the form of colourless crystals of melting point 162.5°–163° C.

(vii) 2.0 g of rac-3'-(1,1-ethylenedioxyethyl)-1',2',3',4'-tetrahydro-3'-hydroxy-5',8'-dimethoxyspiro[1,3-dithiolane-2,1'-naphthalene] in 20 ml of tetrahydrofuran were added over a period of 10 minutes to a suspension of 6.4 g of mercuric oxide and 6.4 g of mercuric chloride in 200 ml of methanol and 18 ml of water. The resulting suspension was stirred at room temperature for 1.25 hours and then ca 100 ml of solvent were removed by evaporation under reduced pressure. 300 ml of dichloromethane were added and the suspension obtained was filtered to remove insoluble mercury salts. The filtrate was washed with three 200 ml portions of water, dried over magnesium sulphate and evaporated to give a solid residue. Trituration with diethyl ether gave 1.42 g (89%) of rac-3-(1,1-ethylenedioxyethyl)-1,2,3,4-tetrahydro-3-hydroxy-5,8-dimethoxy-1-oxo-naphthalene in the form of an off-white powder of melting point 177.5°–178° C.

(viii) 6.1 g of rac-3-(1,1-ethylenedioxyethyl)-1,2,3,4-tetrahydro-3-hydroxy-5,8-dimethoxy-1-oxo-naphthalene were dissolved in 32 ml of dry tetrahydrofuran and 1.2 g of lithium borohydride were added. The mixture obtained was stirred at room temperature under an atmosphere of nitrogen for 3.5 hours and then a further 400 mg of lithium borohydride were added. After 30 minutes, the solvent was evaporated and the residue was taken up in 100 ml of ethyl acetate and 100 ml of 5% aqueous ammonium chloride. The aqueous layer was extracted with three 50 ml portions of ethyl acetate and the combined extracts were washed with brine, dried and evaporated. The oily residue was dissolved in 200 ml of dry ethyl acetate and 1.8 g of benzeneboronic acid and 10 drops of acetic acid were added. The mixture was heated under reflux in a nitrogen atmosphere for 1 hour, cooled, washed with 10% potassium hydrogen carbonate solution, dried and evaporated. The product was separated on a silica gel column (2.5 cm×20 cm) using hexane/ethyl acetate [(1:1), 75 ml fractions] for the first 12 fractions and then ethyl acetate. 4.3 g (55%) of rac-cis-3-(1,1-ethylenedioxyethyl)-1,2,3,4-tetrahydro-5,8-dimethoxynaphthalene-1,3-diyl benzeneboronate of melting point 149°–149.5° C. were obtained from fractions 2–8 and 1.8 g (29.5%) of rac-trans-3-(1,1-ethylenedioxyethyl)-1,2,3,4-tetrahydro-5,8-dimethoxynaphthalene-1,3-diol of melting point 125.5°–126° C. were obtained from fractions 10–16.

(ix) 62 mg of rac-trans-3-(1,1-ethylenedioxyethyl)-1,2,3,4-tetrahydro-5,8-dimethoxynaphthalene-1,3-diol and 30 mg of benzeneboronic acid were dissolved in 10 ml of benzene and 5 mg of toluene-4-sulphonic acid were added while stirring. The resulting mixture was left to stand at room temperature overnight and was then washed with 5 ml of 10% potassium hydrogen carbonate solution. After drying, the solvent was evaporated and the residue was triturated with diethyl ether/hexane to give 63 mg (79.5%) of rac-cis-3-(1,1-ethylenedioxyethyl)-1,2,3,4-tetrahydro-5,8-dimethoxynaphthalene-1,3-diyl benzeneboronate which was identical with the compound obtained according to the preceding paragraph.

(x) 4.3 g of rac-cis-3-(1,1-ethylenedioxyethyl)-1,2,3,4-tetrahydro-5,8-dimethoxynaphthalene-1,3-diyl benzeneboronate were dissolved in 22 ml of dichloromethane containing 1 ml of acetic acid. 22 ml of 2-methyl-2,4-pentanediol were added and the resulting solution was left to stand at room temperature for 30 hours. The mixture was poured into 100 ml of 5% potassium hydrogen carbonate solution and extracted with four 100 ml portions of dichloromethane. The combined extracts were dried over magnesium sulphate and evaporated to give a colourless oil which was dissolved in 100 ml of hexane. The solution was seeded and the product was allowed to crystallise at 4° C. overnight. The product was collected and dried in vacuo to give 2.65 g (79%) of rac-cis-3-(1,1-ethylenedioxyethyl)-1,2,3,4-tetrahydro-5,8-dimethoxynaphthalene-1,3-diol of melting point 127°-127.5° C.

(xi) A solution of 7.33 g of ammonium ceric nitrate in 100 ml of water was added over a period of 5 minutes to a stirred solution of 2.06 g of rac-cis-3-(1,1-ethylenedioxyethyl)-1,2,3,4-tetrahydro-5,8-dimethoxynaphthalene-1,3-diol in 100 ml of acetonitrile. After a further 5 minutes, the mixture was poured into 500 ml of water and the product was extracted with six 150 ml portions of dichloromethane. The combined dichloromethane extracts were dried over magnesium sulphate and evaporated to give 2.0 g of rac-cis-3-(1,1-ethylenedioxyethyl)-1,2,3,4,5,8-hexahydro-5,8-dioxonaphthalene-1,3-diol in the form of an orange gum which was dissolved in 150 ml of xylene and used directly in the next step.

(xii) 2.5 g of trans-1,2-diacetoxy-1,2-dihydrobenzocyclobutene were added to the solution of rac-cis-3-(1,1-ethylenedioxyethyl)-1,2,3,4,5,8-hexahydro-5,8-dioxonaphthalene-1,3-diol in xylene, prepared as described in the preceding paragraph, and the mixture was heated at 140° C. under an atmosphere of nitrogen for 1.75 hours. The solution was cooled and the solvent was evaporated to give a yellow crystalline product which was washed with diethyl ether and filtered to give 2.12 g (84%) of rac-cis-3-(1,1-ethylenedioxyethyl)-1,2,3,4,5,12-hexahydro-5,12-dioxonaphthacene-1,3-diol in the form of yellow crystals of melting point 217°-218° C. Recrystallisation from tetrahyfrofuran/isopropanol raised the melting point to 221°-223° C.

EXAMPLE 2

(A) In a manner analogous to that described in Example 1(A), from (1R)-cis-3-acetyl-1,2,3,4,5,12-hexahydro-5,12-dioxonaphthacene-1,3-diol there was obtained (1R)-cis-3-acetyl-1,2,3,4,5,12-hexahydro-5,12-dioxo-1,3-naphthacenediyl benzeneboronate in the form of a yellow solid of melting point 245°-246° C.; $[\alpha]_D^{20} = -120.8°$ (c=0.54 in dioxan).

(B) In a manner analogous to that described in Example 1(B), from (1R)-cis-3-acetyl-1,2,3,4,5,12-hexahydro-5,12-dioxo-1,3-naphthacenediyl benzeneboronate there was obtained (1R)-cis-5,12-diacetoxy-3-acetyl-1,2,3,4-tetrahydro-1,3-naphthacenediyl benzeneboronate in the form of off-white crystals of melting point 276°-278° C.; $[\alpha]_D^{20} = -257.1°$ (c=0.5% in dioxan).

(C) Oxidation of (1R)-cis-5,12-diacetoxy-3-acetyl-1,2,3,4-tetrahydro-1,3-naphthacenediyl benzeneboronate in a manner analogous to that described in Example 1(C) yielded (1R)-cis-5,12-diacetoxy-3-acetyl-1,2,3,4,6,11-hexahydro-6,11-dioxo-1,3-naphthacenediyl benzeneboronate in the form of off-white crystals of melting point 194°-199° C.; $[\alpha]_D^{20} = -173.3°$ (c=0.5% in dioxan).

(D) (1R)-cis-5,12-diacetoxy-3-acetyl-1,2,3,4,6,11-hexahydro-6,11-dioxo-1,3-naphthacenediyl benzeneboronate was treated with boron trichloride in a manner analogous to that described in Example 1(D) to give (1R)-cis-3-acetyl-1,2,3,4,6,11-hexahydro-5,12-dihydroxy-6,11-dioxo-1,3-naphthacenediyl benzeneboronate in the form of orange crystals of melting point 223°-224° C.; $[\alpha]_D^{20} = -350.4°$ (c=0.1% in dioxan).

(E) In a manner analogous to that described in Example 1(E), from (1R)-cis-3-acetyl-1,2,3,4,6,11-hexahydro-5,12-dihydroxy-6,11-dioxo-1,3-naphthacenediyl benzeneboronate there was obtained (1R)-cis-3-acetyl-1,2,3,4,6,11-hexahydro-1,3,5,12-tetrahydroxy-6,11-dioxonaphthacene in the form of red crystals of melting point 176.5°-178.5° C.; $[\alpha]_D^{20} = -161.5°$ (c=0.1% in dioxan).

The (1R)-cis-3-acetyl-1,2,3,4,5,12-hexahydro-5,12-dioxonaphthacene-1,3-diol used as the starting material in part (A) of this Example can be prepared as follows:

(i) A suspension of 3.42 g of rac-1',2',3',4'-tetrahydro-2'-hydroxy-5',8'-dimethoxyspiro[1,3-dithiolane-2,4'-naphthalene]-2'-carboxylic acid [prepared as described in Example 1(iii)] and 4.0 g of brucine was heated under reflux until a clear solution was obtained. After seeding, the solution was left to cool slowly to room temperature. The crystalline precipitate (3.6 g) was collected after 2 days.

The precipitate was dissolved in 1500 ml of boiling ethyl acetate, the solution was concentrated to 600 ml and left to cool slowly. The crystalline product [2.7 g $[\alpha]_D^{20} = -46.6°$, c=0.5% in dimethylformamide] was suspended in 150 ml of ethyl acetate and shaken with three 10 ml portions of 5-M hydrochloric acid and with two 100 ml portions of brine. After drying over magnesium sulphate, the solvent was evaporated to give a colourless oil which was crystallised from diethyl ether to yield 1.22 g of (R)-1',2',3',4'-tetrahydro-2'-hydroxy-5',8'-dimethyoxyspiro]1,3-dithiolane-2,4'-naphthalene]-2'-carboxylic acid in the form of colourless crystals of melting point 147°-149° C.; $[\alpha]_D^{20} = +13.8°$ (c=0.5% in dioxan).

(ii) According to the procedure described in Example 1(iv), the foregoing acid was converted into methyl (R)-1',2',3',4'-tetrahydro-2'-hydroxy-5',8'-dimethoxyspiro[1,3-dithiolane-2,4'-naphthalene]-2'-carboxylate in the form of colourless crystals of melting point 118°-120° C.; $[\alpha]_D^{20} = +13.0°$ (c=0.5% in chloroform).

(iii) According to the procedure described in Example 1(v), from the foregoing methyl ester there was obtained (R)-3'-acetyl-1',2',3',4'-tetrahydro-3'-hydroxy-5',8'-dimethoxyspiro[1,3-dithiolane-2,1'-naphthalene] in 53% yield in the form of colourless crystals of melting point 178°-180° C.; $[\alpha]_D^{20} = +23.7°$ (c=0.5% in chloroform);

(iv) By ketalising the foregoing methyl ketone in a manner analogous to that described in Example 1(vi) there was obtained (R)-3'-(1,1-ethylenedioxyethyl)-

1′,2′,3′,4′-tetrahydro-3′-hydroxy-5′,8′-dimethoxys-piro[1,3-dithiolane-2,1′-naphthalene] of melting point 143°–145° C.; $[\alpha]_D^{20} = +42.6°$ (c=0.5% in chloroform).

(v) The foregoing ketal was treated with a mixture of mercuric oxide and mercuric chloride in a manner analogous to that described in Example 1(vii) to give (R)-3-(1,1-ethylenedioxyethyl)-1,2,3,4-tetrahydro-3-hydroxy-5,8-dimethoxy-1-oxo-naphthalene of melting point 183°–184° C.; $[\alpha]_D^{20} = -12.9°$ (c=0.5% in chloroform).

(vi) According to the procedure described in Example 1(viii), from the compound prepared according to the preceding paragraph there was obtained (1R)-cis-3-(1,1-ethylenedioxyethyl)-1,2,3,4-tetrahydro-5,8-dimethoxynaphthalene-1,3-diyl benzeneboronate of melting point 124°–125° C.; $[\alpha]_D^{20} = -37.7°$ (c=0.5% in chloroform).

(vii) According to the procedure described in Example 1(x), from the foregoing benzeneboronate there was obtained (1R)-cis-3-(1,1-ethylenedioxyethyl)-1,2,3,4-tetrahydro-5,8-dimethoxynaphthalene-1,3-diol of melting point 143.5°–144.5° C.; $[\alpha]_D^{20} = -5.7°$ (c=0.5% in chloroform).

(viii) According to the procedure described in Example 1(xi) and (xii), from the foregoing diol there was obtained (1R)-cis-3-(1,1-ethylenedioxyethyl)-1,2,3,4,5,12-hexahydro-5,12-dioxonaphthacene-1,3-diol of melting point 212°–214° C.; $[\alpha]_D^{20} = -26.5°$ (c=0.5% in dioxan).

(ix) 0.5 g of (1R)-cis-3-(1,1-ethylenedioxyethyl)-1,2,3,4,5,12-hexahydro-5,12-dioxonaphthacene-1,3-diol was dissolved in 140 ml of dioxan and 40 ml of concentrated hydrochloric acid and 400 ml of water were added. The mixture was stirred at room temperature for 5 hours and then poured into 400 ml of water. The product was extracted into three 150 ml portions of dichloromethane, the combined dichloromethane extracts were washed with 10% potassium hydrogen carbonate solution, dried and evaporated to give orange-yellow crystals. Recrystallisation from dichloromethane/diethyl ether gave 358 mg (81%) of (1R)-cis-3-acetyl-1,2,3,4,5,12-hexahydro-5,12-dioxonaphthacene-1,3-diol in the form of yellow crystals of melting point 190°–191° C.; $[\alpha]_D^{20} = -66.9°$ (c=0.5% in dioxan).

EXAMPLE 3

(A) In a manner analogous to that described in Example 1(A) from (1R)-cis-3-(1,1-ethylenedioxyethyl)-1,2,3,4,5,12-hexahydro-5,12-dioxonaphthacene-1,3-diol there was obtained (1R)-cis-3-(1,1-ethylenedioxyethyl)-1,2,3,4,5,12-hexahydro-5,12-dioxo-1,3-naphthacenediyl benzeneboronate of melting point 235°–240° C.; $[\alpha]_D^{20} = -126.9°$ (c=0.5% in chloroform).

(B) In a manner analogous to that described in Example 1(B), from (1R)-cis-(1,1-ethylenedioxyethyl)-1,2,3,4,5,12-hexahydro-5,12-dioxo-1,3-naphthacenediyl benzeneboronate there was obtained (1R)-cis-5,12-diacetoxy-3-(1,1-ethylenedioxyethyl)-1,2,3,4-tetrahydro-1,3-naphthacenediyl benzeneboronate of melting point 280°–284° C.; $[\alpha]_D^{20} = -227.4°$ (c=0.2% in chloroform).

(C) (1R)-cis-5,12-diacetoxy-3-(1,1-ethylenedioxyethyl)-1,2,3,4-tetrahydro-1,3-naphthacenediyl benzeneboronate was oxidised in a manner analogous to that described in Example 1(C) to give (1R)-cis-5,12-diacetoxy-3-(1,1-ethylenedioxyethyl)-1,2,3,4,6,11-hexahydro-6,11-dioxo-1,3-naphthacenediyl benzeneboronate which was used without further purification.

(D) Treatment of (1R)-cis-5,12-diacetoxy-3-(1,1-ethylenedioxyethyl)-1,2,3,4,6,11-hexahydro-6,11-dioxo-1,3-naphthacenediyl benzeneboronate with boron trichloride in a manner analogous to that described in Example 1(D) yielded (1R,3R)-cis-3-acetyl-1,2,3,4,6,11-hexahydro-5,12-dihydroxy-6,11-dioxo-1,3-naphthacenediyl benzeneboronate which was identical with the product obtained according to Example 2(D) and which was converted into (1R)-cis-3-acetyl-1,2,3,4,6,11-hexahydro-1,3,5,12-tetrahydroxy-6,11-dioxonaphthacene in a manner analogous to that described in Example 1(E).

The (1R)-cis-3-(1,1-ethylenedioxyethyl)-1,2,3,4,5,12-hexahydro-5,12-dioxonaphthacene-1,3-diol used as the starting material in part (A) of this Example can be prepared as described in Example 2(viii).

EXAMPLE 4

(A) In a manner analogous to that described in Example 1(A), from (1S)-cis-3-acetyl-1,2,3,4,5,12-hexahydro-5,12-dioxonaphthacene-1,3-diol there was obtained (1S)-cis-3-acetyl-1,2,3,4,5,12-hexahydro-5,12-dioxo-1,3-naphthacenediyl benzeneboronate in the form of yellow crystals of melting point 246°–247° C.; $[\alpha]_D^{20} = -120.7°$ (c=0.5% in dioxan).

(B) In a manner analogous to that described in Example 1(B), from (1S)-cis-3-acetyl-1,2,3,4,5,12-hexahydro-5,12-dioxo-1,3-naphthacenediyl benzeneboronate there was obtained (1S)-cis-5,12-diacetoxy-3-acetyl-1,2,3,4-tetrahydro-1,3-naphthacenediyl benzeneboronate in the form of off-white crystals of melting point 271.5°–272° C.; $[\alpha]_D^{20} = -263.1°$ (c=0.5% in dioxan).

(C) Oxidation of (1S)-cis-5,12-diacetoxy-3-acetyl-1,2,3,4-tetrahydro-1,3-naphthacenediyl benzeneboronate in a manner analogous to that described in Example 1(C) yielded (1S)-cis-5,12-diacetoxy-3-acetyl-1,2,3,4,6,11-hexahydro-6,11-dioxo-1,3-naphthacenediyl benzeneboronate in the form of off-white crystals of melting point 191°–200° C. $[\alpha]_D^{20} = +171.3°$ (c=0.5% in dioxan).

(D) (1S)-cis-5,12-diacetoxy-3-acetyl-1,2,3,4,6,11-hexahydro-6,11-dioxo-1,3-naphthacenediyl benzeneboronate was treated with boron trichloride in a manner analogous to that described in Example 1(D) to give (1S)-cis-3-acetyl-1,2,3,4,6,11-hexahydro-5,12-dihydroxy-6,11-dioxo-1,3-naphthacenediyl benzeneboronate in the form of orange crystals of melting point 220°–222° C.; $[\alpha]_D^{20} = +353.3°$ (c=0.1% in dioxan).

(E) In a manner analogous to that described in Example 1(E), from (1S)-cis-3-acetyl-1,2,3,4,6,11-hexahydro-5,12-dihydroxy-6,11-dioxo-1,3-naphthacenediyl benzeneboronate there was obtained (1S)-cis-3-acetyl-1,2,3,4,6,11-hexahydro-1,3,5,12-tetrahydroxy-6,11-dioxonaphthacene in the form of red crystals of melting point 182°–184° C.; $[\alpha]_D^{20} = +164.5°$ (c=0.1% in dioxan).

The (1S)-cis-3-acetyl-1,2,3,4,5,12-hexahydro-5,12-dioxonaphthacene-1,3-diol used as the starting material in part (A) of this Example can be prepared as follows:

(i) The ethyl acetate mother liquors from the first crystallisation of the procedure described in Example 2(i) were shaken with three 10 ml portions of 5-M hydrochloric acid and with two 100 ml portions of brine, dried and evaporated to give 1.7 g of a solid residue. This residue was suspended in 50 ml of ethyl acetate and heated under reflux for 0.5 hour. After cooling, 0.6 g of rac-1′,2′,3′-tetrahydro-2′-hydroxy-5′,8′-dimethoxyspiro[1,3-dithiolane-2,4′-naphthalene]-2′-carboxylic acid of melting point 189°–190° C. was obtained. The mother liquors were evaporated and the residue was taken up in diethyl ether, filtered, and the product crystallised to give 1.12 g of (S)-1',2',3',4'-tetrahydro-2'-hydroxy-5',8'-dimethoxyspiro[1,3-dithiolane-2,4'-naphthalene]-2'-carboxylic acid in the form of colourless crystals of melting point 145°–148° C.; $[\alpha]_D^{20} = -13.5°$ (c=0.5% in dioxan).

(ii) According to the procedure described in Example 1(iv), the foregoing acid was converted into methyl (S)-1',2',3',4'-tetrahydro-2'-hydroxy-5',8'-dimethoxyspiro[1,3-dithiolane-2,4'-naphthalene]-2'-carboxylate in the form of colourless crystals of melting point 115°–117° C.; $[\alpha]_D^{20} = -12.7°$ (c=0.5% in chloroform).

(iii) According to the procedure described in Example 1(v), from the foregoing methyl ester there was obtained (S)-3'-acetyl-1',2',3',4'-tetrahydro-3'-hydroxy-5',8'-dimethoxyspiro[1,3-dithiolane-2,1'-naphthalene] in 52% yield in the form of colourless crystals of melting point 178°–180° C.; $[\alpha]_D^{20} = -23.8°$ (c=0.5% in chloroform).

(iv) Ketalisation of the foregoing methyl ketone in a manner analogous to that described in Example 1(vi) gave (S)-3,-(1,1-ethylenedioxyethyl)-1',2',3',4'-tetrahydro-3'-hydroxy-5',8'-dimethoxyspiro[1,3-dithiolane-2,1'-naphthalene] of melting point 144°–146° C.; $[\alpha]_D^{20} = -42.4°$ (c=0.5% in chloroform).

(v) The foregoing ketal was treated with a mixture of mercuric oxide and mercuric chloride in a manner analogous to that described in Example 1(vii) to give (S)-3-(1,1-ethylenedioxyethyl)-1,2,3,4-tetrahydro-3-hydroxy-5,8-dimethoxy-1-oxo-naphthalene of melting point 182.5°–184° C.; $[\alpha]_D^{20} = +14.0°$ (c=0.5% in chloroform).

(vi) According to the procedure described in Example 1(viii), from the compound prepared according to the preceding paragraph there was obtained (1S)-cis-3-(1,1-ethylenedioxyethyl)-1,2,3,4-tetrahydro-5,8-dimethoxynaphthalene-1,3-diyl benzeneboronate of melting point 124°–126° C.; $[\alpha]_D^{20} = +36.7°$ (c=0.5% in chloroform).

(vii) According to the procedure described in Example 1(x), from the foregoing benzeneboronate there was obtained (1S)-cis-3-(1,1-ethylenedioxyethyl)-1,2,3,4-tetrahydro-5,8-dimethoxynaphthalene-1,3-diol of melting point 143°–144° C.; $[\alpha]_D^{20} = +6.3°$ (c=0.5% in chloroform).

(viii) According to the procedure described in Example 1(xi) and (xii), from the foregoing diol there was obtained (1S)-cis-3-(1,1-ethylenedioxyethyl)-1,2,3,4,5,12-hexahydro-5,12-dioxonaphthacene-1,3-diol of melting point 215°–216° C.; $[\alpha]_D^{20} = +27.6$ (c=0.5% in dioxan).

(ix) Treatment of the foregoing ketal with dilute hydrochloric acid in dioxan in a manner analogous to that described in Example 2(ix) gave (1S)-cis-3-acetyl-1,2,3,4,5,12-hexahydro-5,12-dioxonaphthacene-1,3-diol of melting point 193°–195° C.; $[\alpha]_D^{20} = +67.6°$ (c=0.5% in dioxan).

EXAMPLE 5

(A) In a manner analogous to that described in Example 1(A), from rac-cis-3-acetoxymethyl-1,2,3,4,5,12-hexahydro-5,12-dioxonaphthacene-1,3-diol there was obtained rac-cis-3-acetoxymethyl-1,2,3,4,5,12-hexahydro-5,12-dioxo-1,3-naphthacenediyl benzeneboronate in the form of yellow crystals of melting point 262°–263° C.

(B) In a manner analogous to that described in Example 1(B), from rac-cis-3-acetoxymethyl-1,2,3,4,5,12-hexahydro-5,12-dioxo-1,3-naphthacenediyl benzeneboronate there was obtained rac-cis-5,12-diacetoxy-3-acetoxymethyl-1,2,3,4-tetrahydro-1,3-naphthacenediyl benzeneboronate in the form of pale yellow crystals of melting point 236°–238° C.

(C) Oxidation of rac-cis-5,12-diacetoxy-3-acetoxymethyl-1,2,3,4-tetrahydro-1,3-naphthacenediyl benzeneboronate in a manner analogous to that described in Example 1(C) gave rac-cis-5,12-diacetoxy-3-acetoxymethyl-1,2,3,4,6,11-hexahydro-6,11-dioxo-1,3-naphthacenediyl benzeneboronate in the form of pale yellow crystals of melting point 199°–200° C.

(D) Treatment of rac-cis-5,12-diacetoxy-3-acetoxymethyl-1,2,3,4,6,11-hexahydro-6,11-dioxo-1,3-naphthacenediyl benzeneboronate with boron trichloride in a manner analogous to that described in Example 1(D) afforded rac-cis-3-acetoxymethyl-1,2,3,4,6,11-hexahydro-5,12-dihydroxy-6,11-dioxo-1,3-naphthacenediyl benzeneboronate in the form of red crystals of melting point 200°–202° C.

(E) In a manner analogous to that described in Example 1(E), from rac-cis-3-acetoxymethyl-1,2,3,4,6,11-hexahydro-5,12-dihydroxy-6,11-dioxo-1,3-naphthacenediyl benzeneboronate there was obtained rac-cis-3-acetoxymethyl-1,2,3,4,6,11-hexahydro-1,3,5,12-tetrahydroxy-6,11-dioxonaphthacene in the form of red crystals of melting point 196°–197° C.

The rac-cis-3-acetoxymethyl-1,2,3,4,5,12-hexahydro-5,12-dioxonaphthacene-1,3-diol used as the starting material in part (A) of this Example can be prepared as follows:

(i) 2.0 g of methyl rac-1',2',3',4'-tetrahydro-2'-hydroxy-5',8'-dimethoxyspiro[1,3-dithiolane-2,4'-naphthalene]-2'-carboxylate, prepared as described in Example 1(iv), were dissolved in 200 ml of dry tetrahydrofuran and 2.0 g of sodium borohydride were added to the solution. The resulting mixture was stirred at room temperature under nitrogen for 20 hours. The solvent was removed by evaporation and 100 ml of 10% ammonium chloride solution were added. The mixture was extracted with three 30 ml portions of ethyl acetate. The extracts were dried and evaporated to give a colourless oil. Crystallisation of this oil from ethyl acetate/petroleum ether gave 1.6 g (87%) of rac-1',2',3',4'-tetrahydro-3'-hydroxy-3'-hydroxymethyl-5',8'-dimethoxyspiro[1,3-dithiolane-2,1'-naphthalene] of melting point 132.5°–133.5° C.

(ii) 1.6 g of rac-1',2',3',4'-tetrahydro-3'-hydroxy-3'-hydroxymethyl-5',8'-dimethoxyspiro[1,3-dithiolane-2,1'-naphthalene] were dissolved in 30 ml of dry pyridine and 1.5 g of acetic anhydride were added to the solution. The mixture was left to stand at room temperature for 20 hours and then poured into ice-cold 5-M sulphuric acid. The resulting mixture was extracted with ethyl acetate, the extracts were washed with water and sodium hydrogen carbonate solution, dried and evaporated to give 1.8 g of rac-3'-acetoxymethyl-1',2',3',4'-tetrahydro-3'-hydroxy-5',8'-dimethoxyspiro[1,3-dithiolane-2,1'-naphthalene] in the form of a colourless oil which was used directly in the next step.

(iii) 1.9 g of rac-3'-acetoxymethyl-1',2',3',4'-tetrahydro-3'-hydroxy-5',8'-dimethoxyspiro[1,3-dithiolane-2,1'-naphthalene] in 40 ml of tetrahydrofuran were added to a stirred suspension of 6.4 g of mercuric chloride and 6.4 g of mercuric oxide in 200 ml of methanol containing 18 ml of water. After standing at room temperature for 1 hour, ca 150 ml of solvent were removed by evaporation under reduced pressure, 200 ml of dichloromethane were added and the resulting suspension was filtered to remove insoluble material. The filtrate was washed with three 200 ml portions of water, dried over magnesium sulphate and evaporated to give a solid residue. Trituration with diethyl ether gave 1.0 g (70%) of rac-3-acetoxymethyl-1,2,3,4-tetrahydro-3-hydroxy-5,8-dimethoxy-1-oxo-naphthalene in the form of an off-white powder of melting point 124°–126° C.

(iv) 1.0 g of rac-3-acetoxymethyl-1,2,3,4-tetrahydro-3-hydroxy-5,8-dimethoxy-1-oxo-naphthalene was dissolved in 100 ml of dry tetrahydrofuran and 750 mg of sodium borohydride were added. The mixture was stirred at room temperature for 2 hours and the solvent was removed by evaporation. 100 ml of 10% ammonium chloride were added and the mixture was extracted with three 50 ml portions of ethyl acetate. The combined ethyl acetate extracts were washed with saturated sodium chloride solution, dried over magnesium sulphate and evaporated to give a clear colourless oil which was dissolved in 100 ml of ethyl acetate. 500 mg of benzeneboronic acid and 1 drop of acetic acid were added and the resulting solution was heated under reflux for 1 hour. After evaporation of the solvent, 500 mg of rac-cis-3-acetoxymethyl-1,2,3,4-tetrahydro-5,8-dimethoxynaphthalene-1,3-diyl benzeneboronate crystallised from diethyl ether in the form of colourless crystals. The mother liquors were evaporated and the residue was dissolved in 50 ml of benzene. After the addition of 25 mg of toluene-4-sulphonic acid, the solution was stirred at room temperature overnight. The solution was then washed with 10 ml of 10% potassium hydrogen carbonate solution, dried and evaporated. Crystallisation from diethyl ether gave a further 560 mg of the aforementioned benzeneboronate. The total yield was 1.06 g (81.5%); melting point 153°–154° C.

(v) 1.0 g of rac-cis-3-acetoxymethyl-1,2,3,4-tetrahydro-5,8-dimethoxynaphthalene-1,3-diyl benzeneboronate was dissolved in 6 ml of dichloromethane containing 0.5 ml of acetic acid. 6 ml of 2-methyl-2,4-pentanediol were added and the resulting solution was left to stand at room temperature for 24 hours. The mixture was poured into 50 ml of 5% potassium hydrogen carbonate solution and extracted with three 25 ml portions of dichloromethane. The combined extracts were dried over magnesium sulphate and evaporated to give a colourless oil which was dissolved in 50 ml of hexane. The product was allowed to crystallise at 4° C. overnight. Filtration gave 600 mg (77.5%) of rac-cis-3-acetoxymethyl-1,2,3,4-tetrahydro-5,8-dimethoxynaphthalene-1,3-diol in the form of colourless crystals of melting point 106°–107° C.

(vi) A solution of 1.1 g of ammonium ceric nitrate in 20 ml of water was added to a stirred solution of 296 mg of rac-cis-3-acetoxymethyl-1,2,3,4-tetrahydro-5,8-dimethoxynaphthalene-1,3-diol in 20 ml of acetonitrile. After stirring at room temperature for 5 minutes, the mixture was poured into 200 ml of water and extracted with six 50 ml portions of dichloromethane. The combined organic extracts were dried over magnesium sulphate and evaporated to give rac-cis-3-acetoxymethyl-1,2,3,4,5,8-hexahydro-5,8-dioxonaphthalene-1,3-diol in the form of an orange gum which was dissolved in 20 ml of xylene. This solution was used directly in the next step.

(vii) The solution obtained according to the preceding paragraph was treated with 0.3 g of trans-1,2-diacetoxy-1,2-dihydrobenzocyclobutene and the mixture was heated at 140° C. for 2 hours. After cooling, the solution was filtered through silica gel and the solvent was removed by evaporation to give a solid yellow residue. Trituration with ethyl acetate/diethyl ether gave 220 mg (60%) of rac-cis-3-acetoxymethyl-1,2,3,4,5,12-hexahydro-5,12-dioxo-naphthacene-1,3-diol in the form of yellow crystals of melting point 222°–224° C.

EXAMPLE 6

(A) In a manner analogous to that described in Example 1(A), from (1S)-cis-3-acetoxymethyl-1,2,3,4,5,12-hexahydro-5,12-dioxonaphthacene-1,3-diol there was obtained (1S)-cis-3-acetoxymethyl-1,2,3,4,5,12-hexahydro-5,12-dioxo-1,3-naphthacenediyl benzeneboronate in the form of a yellow oil which was used without further purification.

(B) In a manner analogous to that described in Example 1(B), from (1S)-cis-3-acetoxymethyl-1,2,3,4,5,12-hexahydro-5,12-dioxo-1,3-naphthacenediyl benzeneboronate there was obtained (1S)-cis-5,12-diacetoxy-3-acetoxymethyl-1,2,3,4-tetrahydro-1,3-naphthacenediyl benzeneboronate in the form of pale yellow crystals of melting point 256°–258° C.; $[\alpha]_D^{20} = +251.3°$ (c=0.1% in dioxan).

(C) Oxidation of (1S)-cis-5,12-diacetoxy-3-acetoxymethyl-1,2,3,4-tetrahydro-1,3-naphthacenediyl benzeneboronate in a manner analogous to that described in Example 1(C) gave (1S)-cis-5,12-diacetoxy-3-acetoxymethyl-1,2,3,4,6,11-hexahydro-6,11-dioxo-1,3-naphthacenediyl benzeneboronate in the form of pale yellow crystals of melting point 204°–205° C.; $[\alpha]_D^{20} = +180.3°$ (c=0.1% in dioxan).

(D) Treatment of (1S)-cis-5,12-diacetoxy-3-acetoxymethyl-1,2,3,4,6,11-hexahydro-6,11-dioxo-1,3-naphthacenediyl benzeneboronate with boron trichloride in a manner analogous to that described in Example 1(D) gave (1S)-cis-3-acetoxymethyl-1,2,3,4,6,11-hexahydro-5,12-dihydroxy-6,11-dioxo-1,3-naphthacenediyl benzeneboronate in the form of a red semi-solid which was used without further purification.

(E) In a manner analogous to that described in Example 1(E), from (1S)-cis-3-acetoxymethyl-1,2,3,4,6,11-hexahydro-5,12-dihydroxy-6,11-dioxo-1,3-naphthacenediyl benzeneboronate there was obtained (1S)-cis-3-acetoxymethyl-1,2,3,4,6,11-hexahydro-1,3,5,12-tetrahydroxy-6,11-dioxonaphthacene which, after purification by chromatography on silica gel using 5% methanol in toluene, formed red crystals of melting point 201°–203° C.; $[\alpha]_D^{20} = +119.8°$ (c=0.1% in dioxan).

The (1S)-cis-3-acetoxymethyl-1,2,3,4,5,12-hexahydro-5,12-dioxonaphthacene-1,3-diol used as the starting material in part (A) of this Example can be prepared as follows:

(i) Reduction of methyl (S)-1',2',3',4'-tetrahydro-2'-hydroxy-5',8'-dimethoxyspiro[1,3-dithiolane-2,4'-naphthalene]-2'-carboxylate [prepared as described in Example 4(ii)] with sodium borohydride in tetrahydrofuran in a manner analogous to that described in Example 5(i) gave (S)-1',2',3',4'-tetrahydro-3'-hydroxy-3'-hydroxymethyl-5',8'-dimethoxyspiro[1,3-dithiolane-2,1'-naphthalene] in the form of a colourless gum which was used directly in the next step.

(ii) The foregoing hydroxymethyl compound was treated with acetic anhydride in pyridine in a manner analogous to that described in Example 5(ii) to give (S)-3'-acetoxymethyl-1',2',3',4'-tetrahydro-3'-hydroxy-5',8'-dimethoxyspiro[1,3-dithiolane-2,1'-naphthalene] in the form of a colourless oil which was used directly in the next step.

(iii) The foregoing acetoxymethyl compound was treated with a mixture of mercuric chloride and mercuric oxide in a manner analogous to that described in Example 5(iii) to give (S)-3-acetoxymethyl-1,2,3,4-tetrahydro-3-hydroxy-5,8-dimethoxy-1-oxo-naphthalene in the form of an off-white powder which was used in the next step without purification.

(iv) 2.37 g of the foregoing ketone were dissolved in 100 ml of tetrahydrofuran and 2.0 g of sodium borohydride were added. After stirring at room temperature for 2 hours, the solvent was removed by evaporation and 100 ml of 10% ammonium chloride were added. The mixture was extracted with three 100 ml portions of ethyl acetate, the extracts were dried over magnesium sulphate and evaporated to give a colourless gum. This gum was dissolved in 200 ml of ethyl acetate and 2.0 g of benzeneboronic acid and 3 drops of acetic acid were added. The mixture was heated under reflux for 1 hour, the solvent was removed by evaporation and 200 ml of toluene were added. After the addition of 75 mg of toluene-4-sulphonic acid, the solution was stirred at room temperature for 4.5 hours. The solution was washed with 50 ml of 10% potassium hydrogen carbonate solution, dried over magnesium sulphate and evaporated to give crude (S)-3-acetoxymethyl-1,2,3,4-tetrahydro-5,8-dimethoxynaphthalene-1,3-diyl benzeneboronate in the form of a semi-solid residue which was treated with 2-methyl-2,4-pentanediol in a manner analogous to that described in Example 5(v) to give (S)-cis-3-acetoxymethyl-1,2,3,4-tetrahydro-5,8-dimethoxynaphthalene-1,3-diol in the form of colourless crystals of melting point 97°–98° C.; $[\alpha]_D^{20} = -2.6°$ (c=0.5% in chloroform).

(v) The aforementioned diol was treated in a manner analogous to that described in Example 5(vi) and (vii) to give (1S)-cis-3-acetoxymethyl-1,2,3,4,5,12-hexahydro-5,12-dioxonaphthacene-1,3-diol in the form of yellow crystals of melting point 189°–191° C.; $[\alpha]_D^{20} = +40.3°$ (c=0.5% in chloroform).

EXAMPLE 7

(A) In a manner analogous to that described in Example 1(A), from rac-cis-1,2,3,4,5,12-hexahydro-3-methyl-5,12-dioxonaphthacene-1,3-diol there was obtained rac-cis-1,2,3,4,5,12-hexahydro-3-methyl-5,12-dioxo-1,3-naphthacenediyl benzeneboronate in the form of yellow crystals of melting point 267°–270° C.

(B) In a manner analogous to that described in Example 1(B), from rac-cis-1,2,3,4,5,12-hexahydro-3-methyl-5,12-dioxo-1,3-naphthacenediyl benzeneboronate there was obtained rac-cis-5,12-diacetoxy-1,2,3,4-tetrahydro-3-methyl-1,3-naphthacenediyl benzeneboronate in the form of pale yellow crystals of melting point 292°–293.5° C.

(C) Oxidation of rac-cis-5,12-diacetoxy-1,2,3,4-tetrahydro-3-methyl-1,3-naphthacenediyl benzeneboronate in a manner analogous to that described in Example 1(C) gave rac-cis-5,12-diacetoxy-1,2,3,4,6,11-hexahydro-3-methyl-6,11-dioxo-1,3-naphthacenediyl benzeneboronate in the form of off-white crystals of melting point 255°–259° C.

(D) Treatment of rac-cis-5,12-diacetoxyl1,2,3,4,6,11-hexahydro-3-methyl-6,11-dioxo-1,3-naphthacenediyl benzeneboronate with boron trichloride in a manner analogous to that described in Example 1(D) gave rac-cis-1,2,3,4,6,11-hexahydro-5,12-dihydroxy-3-methyl-6,11-dioxo-1,3-naphthacenediyl benzeneboronate in the form of red crystals of melting point 200°–217° C.

(E) In a manner analogous to that described in Example 1(E), from rac-cis-1,2,3,4,6,11-hexahydro-5,12-dihydroxy-3-methyl-6,11-dioxo-1,3-naphthacenediyl benzeneboronate there was obtained rac-cis-1,2,3,4,6,11-hexahydro-1,3,5,12-tetrahydroxy-3-methyl-6,11-dioxonaphthacene in the form of red crystals of melting point 244°–245° C.

The rac-cis-1,2,3,4,5,12-hexahydro-3-methyl-5,12-dioxonaphthacene-1,3-diol used as the starting material in part (A) of this Example can be prepared as follows:

(i) 326 mg of rac-1',2',3',4'-tetrahydro-3'-hydroxy3'-hydroxymethyl-5',8'-dimethyoxyspiro[1,3-dithiolane-2,1'-naphthalene], prepared as described in Example 5(i), were dissolved in 10 ml of pyridine and the solution was cooled to 0° C. 400 mg of toluene-4-sulphonyl chloride were added and the mixture was held at 4° C. for 20 hours. The solution was poured on to crushed ice, acidified with 5-M sulphuric acid and extracted with ethyl acetate. The ethyl acetate extract was washed with water and then with 5% potassium hydrogen carbonate solution. After drying, the solvent was removed by evaporation to give a white solid. Trituration of this solid with diethyl ether give 400 mg (83%) of rac-1',2',3',4'-tetrahydro-3'-hydroxy-5',8'-dimethoxyspiro[1,3-dithiolane-2,1'-naphthyl]-3'-methyl p-toluenesulphonate in the form of a crystalline powder of melting point 124°–126° C. (decomposition).

(ii) 200 mg of rac-1',2',3',4'-tetrahydro-3'-hydroxy-5',8'-dimethoxyspiro[1,3-dithiolane-2,1'-naphthyl]-3'-methyl p-toluenesulphonate were dissolved in 20 ml of dry tetrahydrofuran containing 100 mg of lithium aluminium hydride. The mixture was heated under reflux for 3.5 hours under a nitrogen atmosphere. The solution was cooled and quenched by the addition of saturated ammonium chloride solution. The solvent was removed by evaporation and the residue was taken up in dilute hydrochloric acid. The solution was extracted with ethyl acetate and the extracts were washed with water, dried and evaporated to give a colourless oil which crystallised from diethyl ethyl. There were obtained 100 mg (77.5%) of rac-1',2',3',4'-tetrahydro-3'-hydroxy-3'-methyl-5',8'-dimethoxyspiro[1,3-dithiolane-2,1'-naphthalene] in the form of colourless crystals of melting point 163°–165° C.

(iii) In a manner analogous to that described in Example 5(iii), from rac-1',2',3',4'-tetrahydro-3'-methyl-5',8'-dimethoxyspiro[1,3-dithiolane-2,1'-naphthalene] there was obtained rac-1,2,3,4-tetrahydro-3-methyl-5,8-dimethoxy-1-oxo-naphthalene which was used without purification.

(iv) In a manner analogous to that described in Example 5(iv), from rac-1,2,3,4-tetrahydro-3-methyl-5,8-dimethoxy-1-oxo-naphthalene there was obtained rac-cis-1,2,3,4-tetrahydro-3-methyl-5,8-dimethoxynaphthalene-1,3-diyl benzeneboronate in the form of colourless crystals of melting point 138°–139° C.

(v) In a manner analogous to that described in Example 5(v), from rac-cis-1,2,3,4-tetrahydro-3-methyl-5,8-dimethoxynaphthalene-1,3-diyl benzeneboronate there was obtained rac-cis-1,2,3,4-tetrahydro-3-methyl-5,8-dimethoxynaphthalene-1,3-diol in the form of colourless crystals of melting poing 142°–144° C.

(vi) In a manner analogous to that described in Example 5 (vi) and (viii), from rac-cis-1,2,3,4-tetrahydro-3-methyl-5,8-dimethoxynaphthalene-1,3-diol there was obtained rac-cis-1,2,3,4,5,12-hexahydro-3-methyl-5,12- dioxonaphthacene-1,3-diol in the form of yellow crystals of melting point 223°–224° C.

EXAMPLE 8

(A) In a manner analogous to that described in Example 1(A), from (1S)-cis-1,2,3,4,5,12-hexahydro-3-methyl-5,12-dioxonaphthacene-1,3-diol there was obtained (1S)-cis-1,2,3,4,5,12-hexahydro-3-methyl-5,12-dioxo-1,3-naphthacenediyl benzeneboronate which was used in the next step without purification.

(B) In a manner analogous to that described in Example 1(B), from (1S)-cis-1,2,3,4,5,12-hexahydro-3-methyl-5,12-dioxo-1,3-naphthacenediyl benzeneboronate there was obtained (1S)-cis-5,12-diacetoxy-1,2,3,4-tetrahydro-3-methyl-1,3-naphthacenediyl benzeneboronate which was used in the next step without purification.

(C) Oxidation of (1S)-cis-5,12-diacetoxy-1,2,3,4-tetrahydro-3-methyl-1,3-naphthacenediyl benzeneboronate in a manner analogous to that described in Example 1(C) gave (1S)-cis-5,12-diacetoxy-1,2,3,4,6,11-hexahydro-3-methyl-6,11-dioxo-1,3-naphthacenediyl benzeneboronate which was used in the next step without purification.

(D) Treatment of (1S)-cis-5,12-diacetoxy-1,2,3,4,6,11-hexahydro-3-methyl-6,11-dioxo-1,3-naphthacenediyl benzeneboronate with boron trichloride in a manner analogous to that described in Example 1(D) gave (1S)-cis-1,2,3,4,6,11-hexahydro-5,12-dihydroxy-3-methyl-6,11-dioxo-1,3-naphthacenediyl benzeneboronate which was used in the next step without purification.

(E) In a manner analogous to that described in Example 1(E), from (1S)-cis-1,2,3,4,6,11-hexahydro-5,12-dihydroxy-3-methyl-6,11-dioxo-1,3-naphthacenediyl benzeneboronate there was obtained (1S)-cis-1,2,3,4,6,11-hexahydro-1,3,5,12-tetrahydroxy-3-methyl-6,11-dioxonaphthacene. Purification by column chromatography on silica gel using 5% methanol in toluene for the elution gave red crystals of melting point 214°–215° C.; $[\alpha]_D^{20}= +152.5°$ (c=0.1% in dioxan).

The (1S)-cis-1,2,3,4,5,12-hexahydro-3-methyl-5,12-dioxonaphthacene-1,3-diol used as the starting material in part (A) of this Example can be prepared as follows:

(i) According to the procedure described in Example 7(i), from (1S)-cis-1',2',3',4'-tetrahydro-3'-hydroxymethyl-5',8'-dimethoxyspiro[1,3-dithiolane-2,1'-naphthalene], prepared as described in Example 6(i), there was obtained (S)-1',2',3',4'-tetrahydro-3'-hydroxy-5',8'-dimethoxyspiro[1,3-dithiolane-2,1'-naphthyl]-3'-methyl p-toluenesulphonate in the form of colourless crystals of melting point above 115° C. (decomposition); $[\alpha]_D^{20}= -37.5°$ (c=0.5% in chloroform).

(ii) Reduction of the foregoing p-toluenesulphonate with lithium aluminium hydride according to the procedure described in Example 6(ii) gave (S)-1',2',3',4'-tetrahydro-3'-hydroxy-3'-methyl-5',8'-dimethoxyspiro[1,3-dithiolane-2,1'-naphthalene] in the form of colourless crystals of melting point 152°–153° C.; $[\alpha]_D^{20}= -48.0°$ (c=0.5% in chloroform).

(iii) The foregoing compound was treated sequentially according to the procedures described in Example 5(iii),(iv) and (v), without purification of the products obtained, to give (S)-cis-1,2,3,4-tetrahydro-3-methyl-5,8-dimethoxynaphthalene-1,3-diol in the form of colourless crystals of melting point 166°–167° C.; $[\alpha]_D^{20}= -7.8°$ (c=0.5% in chloroform).

(iv) The foregoing diol was treated in a manner analogous to that described in Example 5(vi) and 5(vii) to give (1S)-cis-1,2,3,4,5,12-hexahydro-3-methyl-5,12-dioxonaphthacene-1,3-diol in the form of yellow crystals of melting point 209°–211° C.; $[\alpha]_D^{20}= +52.6°$ (c=0.5% in chloroform).

The following Examples illustrate the manner in which the compounds of formula I can be converted into glycosides.

EXAMPLE 9

(A) A solution of 1.0 g of (1S)-cis-3-acetoxymethyl-1,2,3,4,6,11-hexahydro-1,3,5,12-tetrahydroxy-6,11-dioxonaphthacene [prepared as described in Example 6(E)] in 100 ml of tetrahydrofuran was cooled to −5° C. and 1.0 g of 2,3,6-trideoxy-4-O-p-nitrobenzoyl-3-trifluoroacetamido-α-L-lyxopyranosyl chloride was added. The mixture was stirred while a solution of 0.48 g of silver trifluoromethane-sulphonate in 15 ml of dry diethyl ether was added over a period of 20 minutes. After completion of the addition, a further 1.0 g of the aforementioned chlorosugar was added and then a further 0.48 g of silver trifluoromethanesulphonate in 15 ml of dry diethyl ether was added over a period of 20 minutes. The mixture was stirred at −5° C. for 0.5 hour, then poured into 300 ml of 10% potassium hydrogen carbonate solution and extracted with four 100 ml portions of dichloromethane. The dichloromethane extracts were dried over sodium sulphate and evaporated to give a red gum which was purified by column chromatography on silica gel using hexane/ethyl acetate (1:1, vol/vol) for the elution. In addition to 132 mg of unreacted dioxonaphthacene starting material, there were obtained 1.4 g of (1S)-cis-3-acetoxymethyl-1-[(2,3,6-trideoxy-3-trifluoroacetamido-4-O-p-nitrobenzoyl-α-L-lyxohexopyranosyl)oxy]-1,2,3,4,6,11-hexahydro-3,5,12-trihydroxy-6,11-dioxonaphthacene in the form of a red gum which was used without further purification.

(B) 1.4 g of (1S)-cis-3-acetoxymethyl-1-[(2,3,6-trideoxy-3-trifluoroacetamido-4-O-p-nitrobenzoyl-α-L-lyxohexopyranosyl)-oxy]-1,2,3,4,6,11-hexahydro-3,5,12-trihydroxy-6,11-dioxonaphthacene were dissolved in a mixture of 40 ml of dichloromethane and 100 ml of methanol and the resulting solution was cooled to 0° C. 0.1 M aqueous sodium hydroxide solution was added dropwise to produce a permanent brown-purple colour. After 10 minutes, thin-layer chromatography indicated that no starting material remained. The reaction was quenched by the addition of acetic acid to produce an orange-red coloured solution. The mixture was diluted with 250 ml of water and extracted with four 100 ml portions of dichloromethane. The combined dichloromethane extracts were dried over sodium sulphate and evaporated to give an orange gum which was purified by column chromatography using acetone/dichloromethane (1:10 vol/vol) for the elution. Crystallisation from acetone/diethyl ether gave 0.9 g of (1S)-cis-3-acetoxymethyl-1-[(2,3,6-trideoxy-3-trifluoroacetamido-α-L-lyxohexopyranosyl)oxy]-1,2,3,4,6,11-hexahydro-3,5,12-trihydroxy-6,11-dioxonaphthacene in the form of orange-red crystals of melting point 138°–141° C.; $[\alpha]_D^{20}= +170.3°$ (c=0.1% in chloroform).

(C) 0.8 g of (1S)-cis-3-acetoxymethyl-1-[(2,3,6-trideoxy-3-trifluoroacetamido-α-L-lyxohexopyranosyl)oxy]-1,2,3,4,6,11-hexahydro-3,5,12-trihydroxy-6,11-dioxonaphthacene was dissolved in a mixture of 100 ml of dichloromethane and 50 ml of methanol and the solution was cooled to 0° C. 0.1 M aqueous sodium hydroxide was added to produce a deep purple colour.

The solution was allowed to return to room temperature and was stirred for ca 2-2.5 hours until thin-layer chromatography showed that no starting material remained. The reaction was quenched by the addition of acetic acid to restore the orange-red colour, the resulting solution was diluted with 250 ml of water and extracted with four 100 ml portions of dichloromethane. The combined dichloromethane extracts were dried over sodium sulphate and evaporated to give an orange solid. Crystallisation from tetrahydrofuran/diethyl ether gave 0.65 g of (1S)-cis-1-[(2,3,6-trideoxy-3-trifluoroacetamido-α-L-lyxohexopyranosyl)oxy]-1,2,3,4,6,11-hexahydro-3,5,12-trihydroxy-3-hydroxymethyl-6,11-dioxonaphthacene in the form of orange-red crystals of melting point 239°-240° C.; $[\alpha]_D^{20} = +151.6°$ (c=0.1% in chloroform).

(D) 500 mg of (1S)-cis-1-[(2,3,6-trideoxy-3-trifluoroacetamido-α-L-lyxohexopyranosyl)oxy]-1,2,3,4,6,11-hexahydro-3,5,12-trihydroxy-3-hydroxymethyl-6,11-dioxonaphthacene were dissolved in 50 ml of 0.1 M aqueous sodium hydroxide and the solution was stirred at room temperature for 45 minutes. The solution was adjusted to pH 8-9 by the addition of 0.1 M aqueous hydrochloric acid and then repeatedly extracted with dichloromethane containing 10% ethanol until the extracts were virtually colourless. The combined extracts were washed with water, dried over sodium sulphate and evaporated to give a red solid. This solid was dissolved in 10 ml of dichloromethane containing 2 ml of methanol and filtered. 4 ml of 0.25 M methanolic hydrogen chloride were added while swirling and the solution was concentrated to ca 5 ml. After precipitation by the addition of 50 ml of anhydrous diethyl ether, filtration, washing the filter residue with diethyl ether and drying in vacuo, there were obtained 455 mg of (1S)-cis-1-[(3-amino-2,3,6-trideoxy-α-L-lyxohexopyranosyl)oxy]-1,2,3,4,6,11-hexahydro-3,5,12-trihydroxy-3-hydroxymethyl-6,11-dioxonaphthacene hydrochloride in the form of an orange-red solid of melting point 183°-186° C. (decomposition); $[\alpha]_D^{20} = +153.2°$ (c=0.05% in methanol).

EXAMPLE 10

(A) In a manner analogous to that described in Example 9(A), from (1S)-cis-1,2,3,4,6,11-hexahydro-1,3,5,12-tetrahydroxy-3-methyl-6,11-dioxonaphthacene [prepared as described in Example 8(E)] there was obtained, after crystallisation from tetrahydrofuran/hexane, (1S)-cis-[(2,3,5-trideoxy-3-trifluoroacetamido-4-O-p-nitrobenzoyl-α-L-lyxohexopyranosyl)oxy]-1,2,3,4,6,11-hexahydro-3,5,12-trihydroxy-3-methyl-6,11-dioxonaphthacene in the form of orange-red crystals of melting point 225°-226° C.; $[\alpha]_D^{20} = -101.8°$ (c=0.1% in chloroform).

(B) The product obtained according to the preceding paragraph was treated according to the procedure described in Example 9(B) to give (1S)-cis-1-[(2,3,6-trideoxy-3-trifluoroacetamido-α-L-lyxohexopyranosyl)oxy]-1,2,3,4,6,11-hexahydro-3,5,12-trihydroxy-3-methyl-6,11-dioxonaphthacene in the form of orange-red crystals of melting point 253°-254° C.; $[\alpha]_D^{20} = +180.9°$ (c=0.1% in chloroform).

(C) The product obtained according to the preceding paragraph was treated according to the procedure described in Example 9(D) to give (1S)-cis-1-[(3-amino-2,3,6-trideoxy-α-L-lyxohexopyranosyl)oxy]-1,2,3,4,6,11-hexahydro-3,5,12-trihydroxy-3-methyl-6,11-dioxonaphthacene hydrochloride in the form of orange-red crystals of melting point 174°-176° C. (decomposition); $[\alpha]_D^{20} = +160.1°$ (c=0.05% in methanol).

What is claimed:

1. A process for the manufacture of compounds of the formula

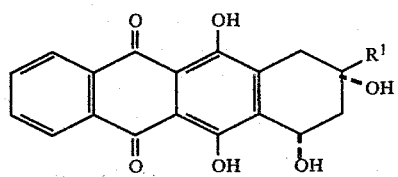

wherein $R^1$ is selected from the group consisting of an esterified carboxy group and a group of the formula

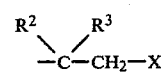

in which $R^2$ and $R^3$ together are an oxo group or a ketal or thioketal group and X is selected from the group consisting of a hydrogen atom, a hydroxy group, an acyloxy group, and

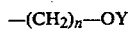

in which n stands for 1 or 2 and Y is selected from the group consisting of a hydrogen atom, lower alkyl and an acyl group,
which process comprises subjecting a compound of the formula

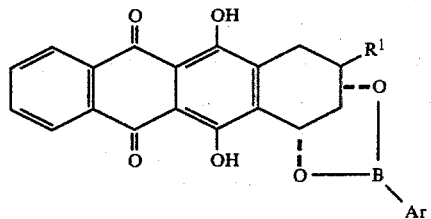

wherein $R^1$ is as above and Ar represents an aryl group, to an ester exchange with a 1,3-diol.

2. The process of claim 1, wherein the 1,3-diol is 2-methyl-2,4-pentanediol.

3. The process of claim 1, wherein the compound of formula II is prepared by deacylating a compound of the formula

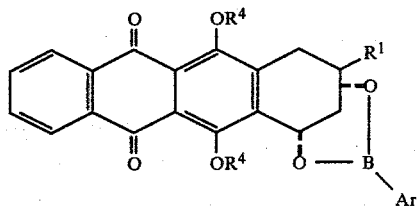

wherein $R^4$ represents an acyl group.

4. The process of claim 3 wherein the deacylation comprises reacting the compound of formula III with boron trichloride in an inert organic solvent at from about −70° to room temperature.

5. The process of claim 3 wherein the compound of formula III is prepared which comprises reacting a compound of the formula

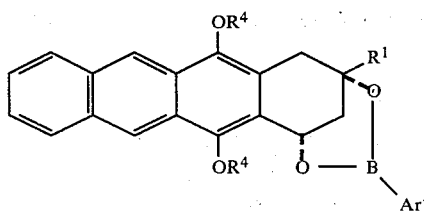

wherein $R^4$, $R^1$ and Ar are as in claim 3 with chromium trioxide in a mixture of a lower alkyl carboxylic acid and its corresponding anhydride.

6. The process of claim 5, wherein the compound of formula IV is prepared by catalytically hydrogenating a compound of the formula

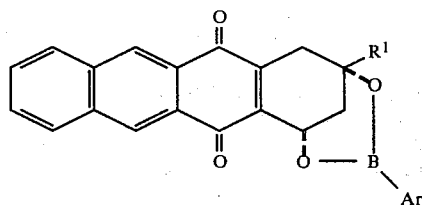

under acylating conditions.

7. The process of claim 6, wherein the compound of formula V is prepared by reacting a compound of the formula

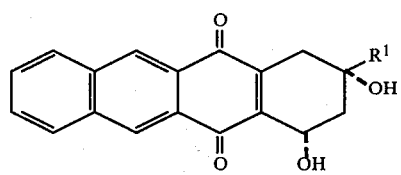

with an aromatic boronic acid.

8. The process according to claim 1 wherein $R^1$ is as in claim 1 with the limitation that in the group (a) $R^2$ and $R^3$ together are ketal or thioketal groups when X represents a hydrogen atom or a hydroxy group.

9. A compound of the formula

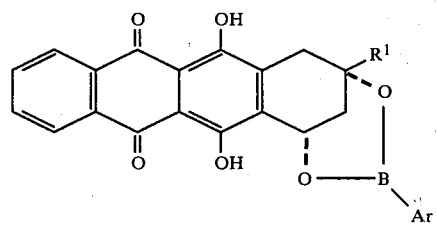

wherein $R^1$ is selected from the group consisting of lower alkyl, an esterified carboxy group and a group of the formula

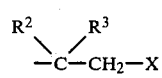

in which $R^2$ and $R^3$ together are an oxo group or a ketal or thioketal group and X is selected from the group consisting of a hydrogen atom, a hydroxy group, an acyloxy group, and $$-(CH_2)_n-OY \qquad (b)$$

in which n stands for 1 or 2 and Y is selected from the group consisting of a hydrogen atom, lower alkyl and an acyl group, and Ar represents an aryl group.

10. A compound of the formula

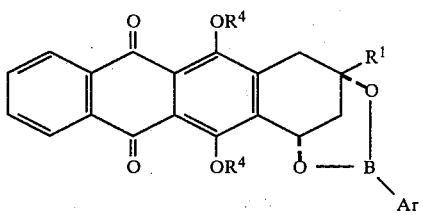

wherein $R^1$ is selected from the group consisting of an esterified carboxy group and a group of the formula

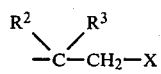

in which $R^2$ and $R^3$ together are an oxo group or a ketal or thioketal group and X is selected from the group consisting of a hydrogen atom, a hydroxy group, an acyloxy group, and $$-(CH_2)_n-OY \qquad (b)$$

in which n stands for 1 or 2 and Y is selected from the group consisting of a hydrogen atom, lower alkyl and an acyl group, Ar represents an aryl group and $R^4$ represents an acyl group.

11. A compound of the formula

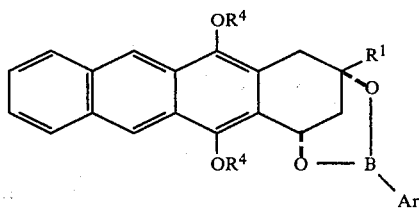

wherein $R^1$ is selected from the group consisting of lower alkyl, an esterified carboxy group and a group of the formula

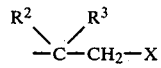

in which $R^2$ and $R^3$ together are an oxo group or a ketal or thioketal group and X is selected from the group consisting of a hydrogen atom, a hydroxy group, an acyloxy group, and $$-(CH_2)_n-OY \qquad (b)$$

in which n stands for 1 or 2 and Y is selected from the group consisting of a hydrogen atom, lower alkyl and an acyl group, Ar represents an aryl group and $R^4$ represents an acyl group.

* * * * *